US009919094B2

(12) United States Patent
Shimazaki et al.

(10) Patent No.: US 9,919,094 B2
(45) Date of Patent: Mar. 20, 2018

(54) CARTRIDGE SET FOR MANUFACTURING SYRINGE AND METHOD FOR MANUFACTURING DUAL-CHAMBER TYPE COMBINED CONTAINER-SYRINGE

(71) Applicant: ARTE CORPORATION, Tokyo (JP)

(72) Inventors: Seiji Shimazaki, Takahagi (JP); Makoto Kakiuchi, Takahagi (JP); Teruo Matsuda, Soka (JP)

(73) Assignee: ARTE CORPORATION, Tokyo (JP)

( * ) Notice: Subject to any disclaimer, the term of this patent is extended or adjusted under 35 U.S.C. 154(b) by 643 days.

(21) Appl. No.: 13/921,019

(22) Filed: Jun. 18, 2013

(65) Prior Publication Data

US 2013/0341849 A1 Dec. 26, 2013

(30) Foreign Application Priority Data

Jun. 20, 2012 (JP) ................. 2012-138770

(51) Int. Cl.
*A61M 5/28* (2006.01)
*A61M 5/00* (2006.01)
(Continued)

(52) U.S. Cl.
CPC ............ *A61M 5/002* (2013.01); *A61M 5/008* (2013.01); *A61M 5/19* (2013.01); *A61M 5/2448* (2013.01);
(Continued)

(58) Field of Classification Search
CPC ........ A61M 5/19; A61M 5/008; A61M 5/284; A61M 5/002; A61M 5/2448; B65B 7/161;
(Continued)

(56) References Cited

U.S. PATENT DOCUMENTS 4,729,208 A * 3/1988 Galy et al. ............ 53/432
4,774,772 A 10/1988 Vetter
(Continued)

FOREIGN PATENT DOCUMENTS

CN 1750852 3/2006
CN 1933862 3/2007
(Continued)

OTHER PUBLICATIONS

European Search Report for European Application No. 13171851.2, dated Sep. 11, 2013.
(Continued)

*Primary Examiner* — Christopher M Koehler
*Assistant Examiner* — Joel Crandall
(74) *Attorney, Agent, or Firm* — Nixon Peabody LLP; Jeffrey L. Costellia

(57) ABSTRACT

A cartridge set including: a plurality of cartridges; a plurality of holders, each of which has an upper end externally fitted to the outer peripheral surface of each of the cartridges, and has a lower end face whose outer diameter is greater than the outer diameter of the outer peripheral surface of the cartridge; a supporting plate that has a plurality of through-holes, each of which has an inner diameter greater than the outer diameter of the outer peripheral surface of the cartridge and has each of the plurality of cartridges inserted therethrough; a storage box that stores the supporting plate therein; and a lid member that blocks an upper end opening of the storage box.

7 Claims, 26 Drawing Sheets

(51) Int. Cl.
   B65B 3/00    (2006.01)
   F26B 5/06    (2006.01)
   A61M 5/19    (2006.01)
   A61M 5/24    (2006.01)
   B65B 63/08   (2006.01)
   B65B 7/16    (2006.01)
   B65B 7/28    (2006.01)
   B65B 31/00   (2006.01)

(52) U.S. Cl.
   CPC .............. *A61M 5/284* (2013.01); *B65B 3/003* (2013.01); *B65B 7/161* (2013.01); *B65B 7/2821* (2013.01); *B65B 63/08* (2013.01); *F26B 5/06* (2013.01); *B65B 31/00* (2013.01); *B65B 2220/14* (2013.01); *B65B 2220/24* (2013.01); *B65B 2230/02* (2013.01); *Y10T 29/49826* (2015.01)

(58) Field of Classification Search
   CPC ..... B65B 63/08; B65B 2230/02; B65B 3/003; B65B 2220/24; B65B 7/2821; B65B 31/00; B65B 2220/14; Y10T 29/49826; F26B 5/06
   See application file for complete search history.

(56) References Cited

U.S. PATENT DOCUMENTS

| | | | | |
|---|---|---|---|---|
| 4,792,329 A | * | 12/1988 | Schreuder | 604/90 |
| 4,851,702 A | * | 7/1989 | Perlman | G21F 5/015 250/506.1 |
| 5,456,360 A | * | 10/1995 | Griffin | B01L 9/06 206/443 |
| 6,164,044 A | * | 12/2000 | Porfano | B65B 55/10 422/28 |
| 7,169,361 B2 | * | 1/2007 | Arnold, Jr. | B01L 9/543 206/562 |
| 2004/0009609 A1 | | 1/2004 | Yarborough et al. | |
| 2006/0184138 A1 | * | 8/2006 | Shimazaki | A61M 5/3134 604/240 |
| 2006/0189943 A1 | | 8/2006 | Kato et al. | |
| 2007/0129673 A1 | * | 6/2007 | Bassarab et al. | 604/85 |
| 2007/0151882 A1 | * | 7/2007 | Cocheteux et al. | 206/366 |
| 2008/0234632 A1 | | 9/2008 | Hasegawa | |
| 2009/0288977 A1 | * | 11/2009 | Vanderbush | A61M 5/002 206/524.8 |

FOREIGN PATENT DOCUMENTS

| | | |
|---|---|---|
| CN | 1933862 | 9/2008 |
| EP | 1913966 | 4/2008 |
| EP | 2 436 407 | 4/2012 |
| JP | 62-278137 A | 12/1987 |
| JP | 04-046152 B | 7/1992 |
| JP | 2007-151727 A | 6/2007 |
| JP | 2009-183768 A | 8/2009 |
| JP | 2011-160875 A | 8/2011 |
| JP | 2012-100927 A | 5/2012 |
| WO | 2008107961 A1 | 9/2008 |
| WO | 2010081838 A2 | 7/2010 |
| WO | 2011007194 A1 | 1/2011 |
| WO | 2011/019605 | 2/2011 |

OTHER PUBLICATIONS

First Search Report issued in CN Appl. No. 2013102396687 dated Jan. 6, 2015, 7 pages, with English translation.
Notice of Allowance issued in Japanese Patent Application No. 2012-138770, dated Aug. 14, 2012.

* cited by examiner

FIG. 3A
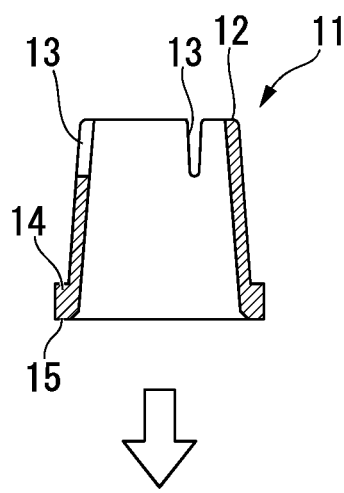
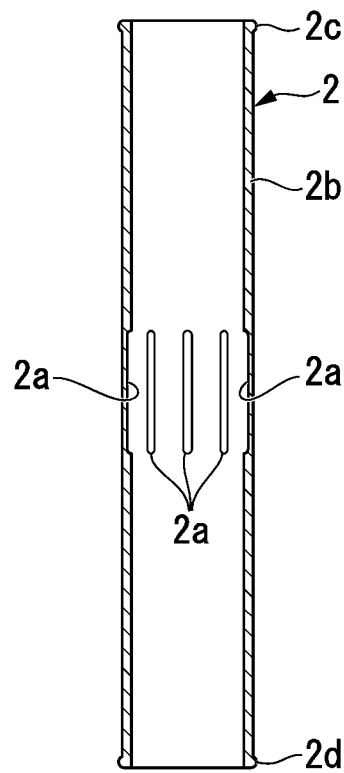
FIG. 3B
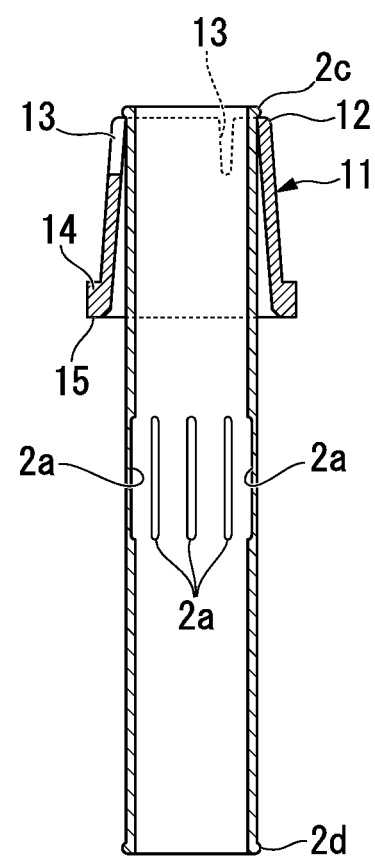

FIG. 7A
FIG. 7B
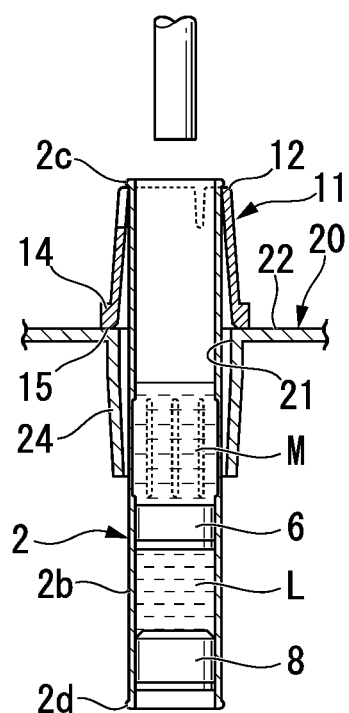
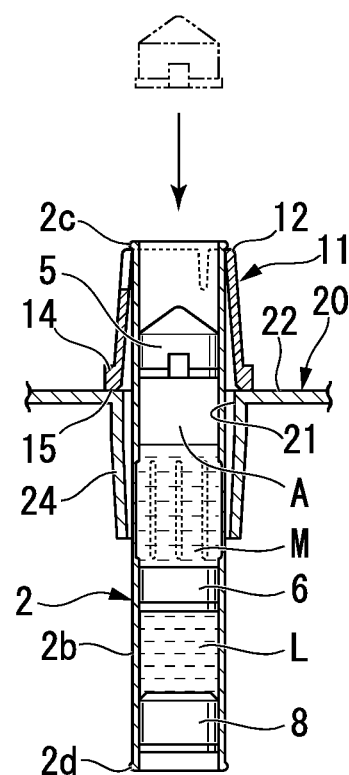

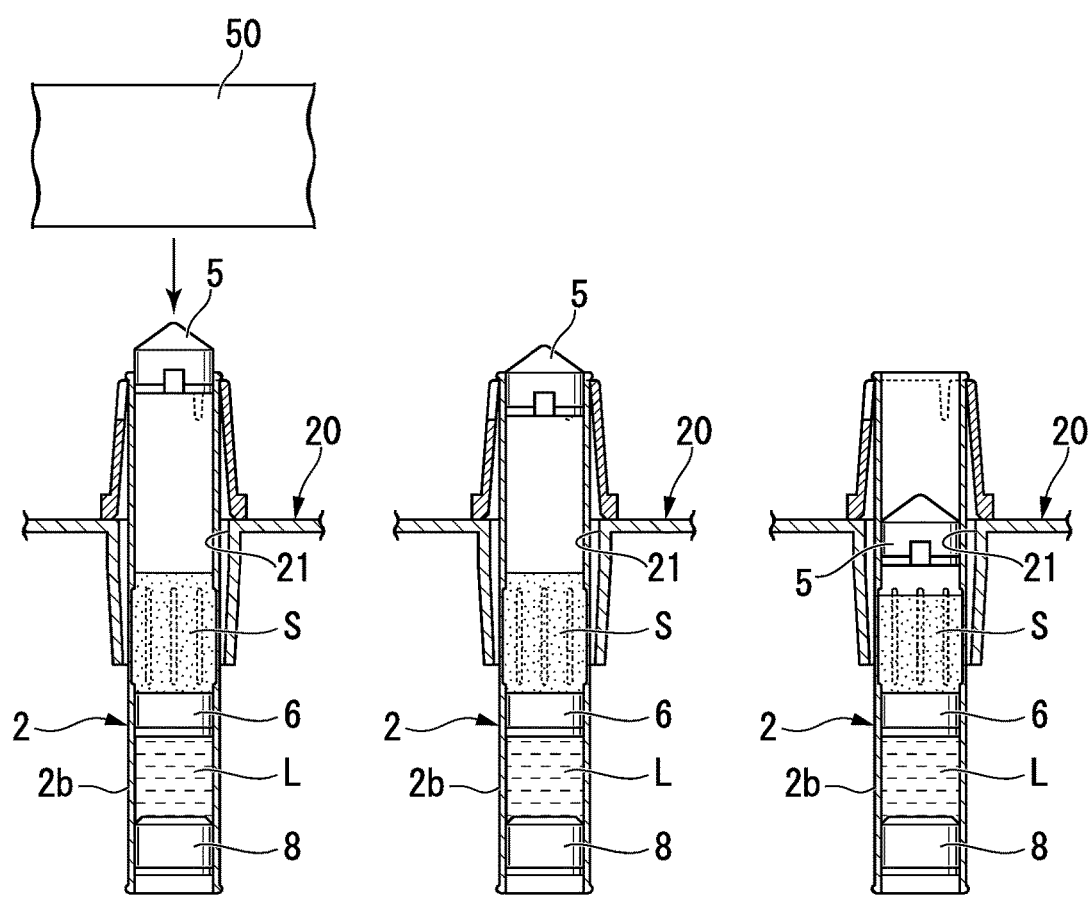

FIG. 10A
FIG. 10B
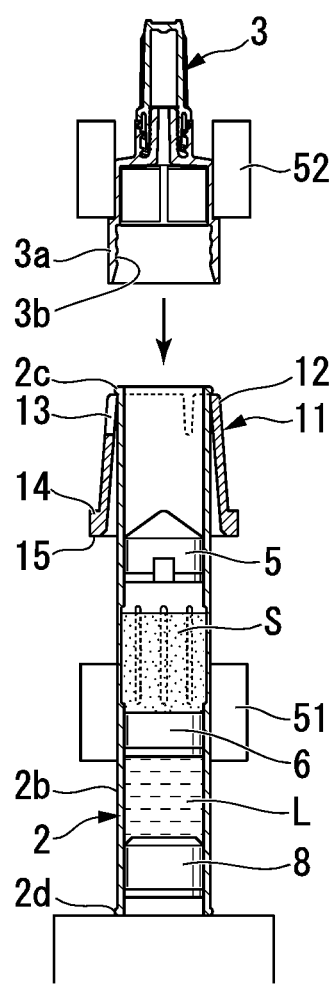
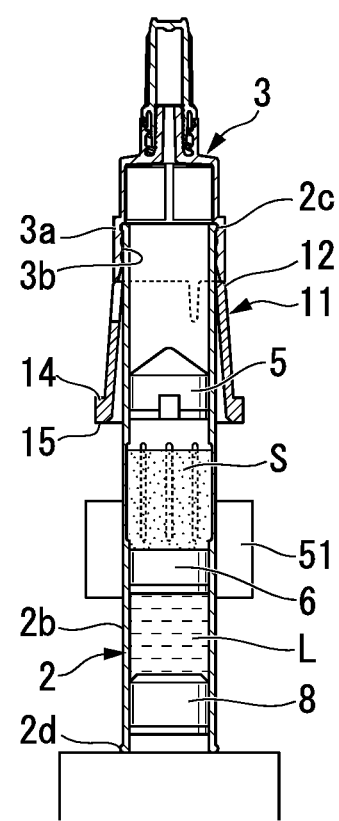

FIG. 11A
FIG. 11B
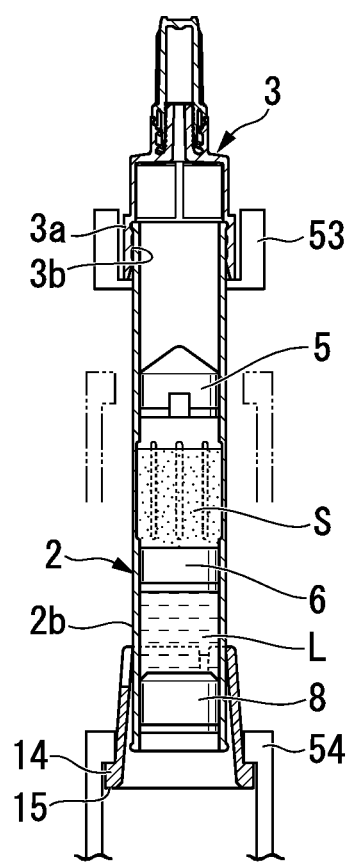
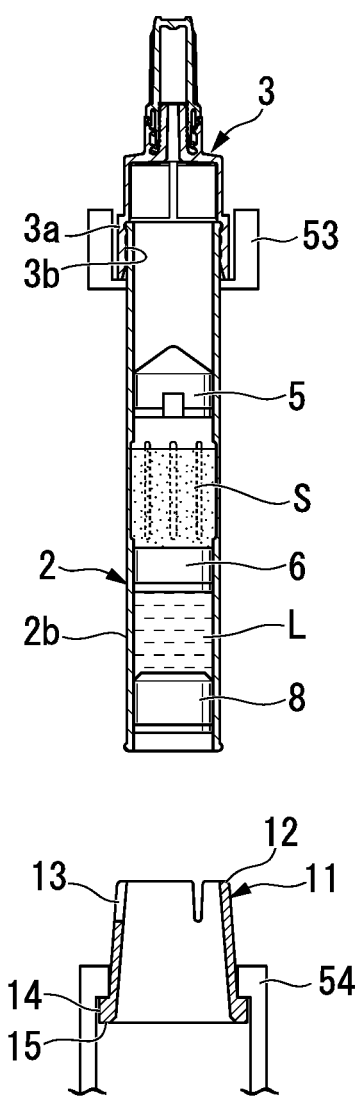

CARTRIDGE SET FOR MANUFACTURING SYRINGE AND METHOD FOR MANUFACTURING DUAL-CHAMBER TYPE COMBINED CONTAINER-SYRINGE

CROSS REFERENCE TO RELATED APPLICATIONS OR PRIORITY CLAIM

This application claims the benefit of Japanese Patent Application No. 2012-138770, filed Jun. 20, 2012, the contents of which are incorporated herein by reference in their entirety.

BACKGROUND OF THE INVENTION

Field of the Invention

The present invention relates to a cartridge set for manufacturing a syringe which stores cartridges to be used when manufacturing a dual-chamber type combined container-syringe and a method for manufacturing a dual-chamber type combined container-syringe using the cartridge set for manufacturing a syringe.

Description of Related Art

Combined container-syringes, which are designed so that an injection preparation is previously filled into the inside of a syringe and an injection can be given immediately to a patient by taking out the syringe from a packing at the time of use, have been widely adopted by medical institutions in all the countries of the world in terms of convenience, safety, and to prevent misuse of an injection drug.

In recent years, so-called dual-chamber type combined container-syringe (for example, refer to Japanese Patent No. 1759157) in which a front chamber is filled with a powder preparation, and a rear chamber is filled with a solvent (suspension) have been in widespread use. As a type that is most widely adopted among them, a syringe that is described in Japanese Patent No. 1759157 is well known.

In this dual-chamber type combined container-syringe, a front assembly made from plastic is fitted to a tip portion of a glass cartridge, and a finger grip is fitted to a rear end portion of the cartridge. A bypass portion that allows the front chamber and the rear chamber to communicate with each other is molded in an intermediate portion of the cylindrical cartridge. The powder preparation filled into the inside of the front chamber is sealed air-tight and liquid-tight by a front stopper and a middle stopper, and the solvent filled into the inside of the rear chamber is sealed air-tight and liquid-tight by the middle stopper and an end stopper. During injection, the end stopper is advanced by pushing a plunger rod screwed to an internal thread provided in a rear portion of the end stopper, and in conjunction with this, the middle stopper inserted in the front end of the rear chamber moves forward along with the solvent within the rear chamber.

Then, when the middle stopper reaches a bypass portion molded on the cartridge, the solvent moves to the front chamber through a gap between the outer peripheral surface of the middle stopper and the bypass portion. In this case, the middle stopper stops at that position until the front face of the end stopper comes into contact with the rear face of the middle stopper. Next, when all of the solvent in the rear chamber has flowed into the front chamber, and the tip of the middle stopper has passed through the bypass portion, the press of the plunger rod is stopped, and an injection drug is adjusted by adequately shaking the overall syringe to sufficiently dissolve (suspend) the powder preparation with the solvent. Thereafter, the plunger rod is pushed in again, and the front stopper that has stopped inside at the tip of the cartridge is made to enter a bypass chamber inside a hub lure lock. Thereby, the seal within the syringe is released by several longitudinal grooves provided in the inner wall of the bypass chamber. Thereafter, after bubbles remaining within the front chamber are discharged, an injection drug is guided to an injection needle through a nozzle head of the hub lure lock in the front assembly utilizing the longitudinal grooves, and the injection drug is administered to a patient.

Here, the dual-chamber type combined container-syringes are delivered to a pharmaceutical company in a state where respective members thereof are not yet assembled. These members are sterilized by the pharmaceutical company, and are sent to and assembled in the following steps, respectively.

That is, after the members are sterilized, the cartridge is put on a filling machine in an aseptic area, and insertion of the sterilized end stopper, filling of the solvent, and insertion of the middle stopper into the cartridge are performed. Thereafter, if necessary, sterilization of the filled solvent by steam sterilization is performed and drying is performed. Then, the front chamber is filled with the powder preparation by a separate filling machine, and the front stopper is inserted into and sealed at the tip portion of the cartridge. Otherwise, a liquid preparation is filled instead of the powder preparation, and the cartridge is put into a lyophilizer to lyophilize the liquid preparation. Then, the front stopper is inserted into and sealed at the tip portion of the cartridge within the lyophilizer. Then, the front assembly is fitted and assembled to the front end of the glass cartridge that has undergone the filling step, and the finger grip is fitted and assembled to the rear end of the cartridge.

Here, in the case of single-chamber type combined container-syringes in which only one kind of injection drug is sealed, empty syringes that are not filled with the injection drug are assembled by a syringe maker and delivered to a pharmaceutical company are common. That is, generally, syringes are delivered to a pharmaceutical company in a state where empty single-chamber type combined container-syringes in which the front assembly and the finger grip are fitted to both ends of the cartridge in advance are regularly aligned in a nest (supporting plate) made of plastics, these syringes are stored in a tub (container), and a lid member, such as nonwoven fabric, is heat-sealed to the top face of the tub.

In addition, the empty single-chamber type combined container-syringes are supported by the nest as the finger grips are caught in through-holes of the nest in a state where the cartridges are inserted through the through-holes of the nest.

In a manufacturing process of a single-chamber type combined container-syringe in a current pharmaceutical company, a method of putting empty single-chamber type combined container-syringes which have been packed by the nest and the tub in a dedicated medical fluid filling and sealing equipment, inserting the front stoppers at high speed, filling an injection drug, and inserting the end stoppers to seal the syringes is widely adopted. Such a method is used for filling, assembling, packing, and the like of various vaccines, and greatly contributes to the adoption and the spreading of the single-chamber type combined container-syringes.

Here, in the case of the dual-chamber type combined container-syringe, the filling of the solvent, the steam sterilization of the solvent after the filling, the aseptic filling of the powder preparation, the adjustment of the filling amount of the solvent or the powder preparation, and the like, are more difficult than the single-chamber type combined container-syringe. Moreover, in the case of the dual-chamber type combined container-syringe, manufacturing steps are complicated and very difficult, such as being required to lyophilize a preparation, and insert and seal the stoppers within the lyophilizer.

When such a difficult steps are performed on a cartridge, constant precision cannot be ensured in a state where the front assembly or the finger grip is fitted to the cartridge. Particularly, if the steam sterilization or the lyophilizing step is performed in a state where the front assembly or the finger grip is fitted, the front assembly or the finger grip may expand or contract, and the precision of assembling, the strength of the syringe or the like may be reduced and deteriorated. Therefore, this is not preferable.

Thus, in the process of manufacturing a dual-chamber type combined container-syringe, it is preferable to perform, on a cartridge as a single body, the step of inserting the various stoppers, the steps of filling and sealing the solvent, the powder preparation, a lyophilizing preparation, or the like, before and after the insertion of the various stoppers. However, in a case where it is intended to support only the cartridge on the supporting plate, since the finger grip is not fitted to the cartridge, the cartridge cannot be supported on the supporting plate with a backlash therebetween. Accordingly, there is a possibility in that fine adjustment, such as position adjustment when the various stoppers or the like are inserted into the cartridge is difficult, and various steps cannot be smoothly performed.

The invention has been made in view of the above circumstances, and an object thereof is to provide a cartridge set for manufacturing a syringe capable of easily and smoothly manufacturing a dual-chamber type combined container-syringe, and a method for manufacturing a dual-chamber type combined container-syringe using the cartridge set for manufacturing a syringe.

SUMMARY OF THE INVENTION

In order to cope with the above circumstances, the invention suggests the following means.

That is, a first aspect of a cartridge set for manufacturing a syringe according to the present invention is a cartridge set including: a plurality of cartridges, each of which extends in an up-and-down direction, forms a cylindrical shape having an outer peripheral surface, and has annular ribs protruding radially outward from opening end portions thereof that correspond to both ends of the outer peripheral surface; a plurality of holders, each of which has flexibility, has an upper end externally fitted to the outer peripheral surface of each of the cartridges, is gradually increased in diameter as it goes downward, and has a lower end face whose outer diameter is greater than the outer diameter of the outer peripheral surface of the cartridge; a supporting plate that forms a plate shape that extends in a horizontal direction, has a plurality of through-holes, each of which has an inner diameter greater than the outer diameter of the outer peripheral surface of the cartridge and has each of the plurality of cartridges inserted therethrough in the up-and-down direction, and has a top face on which the lower end faces of the plurality of holders are placed in a state where the plurality of cartridges are each inserted through the plurality of through-holes in the up-and-down direction; a storage box that forms a box shape that opens upward, stores the supporting plate therein in a state where the supporting plate supports the plurality of cartridges via the plurality of holders, and has a supporting portion which supports an outer edge of the supporting plate; and a lid member that seals an upper end opening of the storage box.

According to the cartridge set for manufacturing a syringe of such a feature, the cartridges are supported by the supporting plate as the lower end faces of the holders fitted onto the outer peripheral surfaces of the cartridges placed on the top face of the supporting plate. In this case, since the inner diameter of the through-hole through which the cartridge is inserted is formed so as to be greater than the outer diameter of the outer peripheral surface of the cartridge, the cartridge can be moved in the horizontal direction within a range of several millimeters within a range of the inner diameter of the through-hole along with the holder.

Additionally, in the first aspect related to the cartridge set for manufacturing a syringe according to the present invention, the holder may have a slit that extends downward from the upper end of the holder.

It is thereby possible to externally fit the holder to the cartridge, or remove the holder from the cartridge easily.

A first aspect of a method for manufacturing a dual-chamber type combined container-syringe according to the present invention is a method for manufacturing a dual-chamber type combined container-syringe using the first aspect of the cartridge set for manufacturing a syringe. This method includes: a first step of taking out the supporting plate along with the plurality of holders and the plurality of cartridges from the cartridge set; a second step of, after the first step, sequentially filling and inserting an end stopper, a solvent, and a middle stopper into each of the plurality of cartridges from above in a state where the plurality of cartridges is supported by the supporting plate via the plurality of holders, and sealing the solvent within the cartridge; and a third step of, after the second step, filling drug and inserting a front stopper into each of the plurality of cartridges from above, and sealing the drug within the cartridge.

According to the method for manufacturing a dual-chamber type combined container-syringe of such a feature, the end stopper, the solvent, the middle stopper, the drug, and the front stopper are inserted into the cartridge by performing the second to third steps on the cartridges supported by the supporting plate via the holders after the supporting plate, the cartridges and the holders are taken out from the storage box. Since the cartridge along with the holder is movable within the horizontal direction within a range of the inner diameter of the through-hole when these steps are performed, position adjustment of the cartridge can be easily performed.

Additionally, in the first aspect related to the method for manufacturing a dual-chamber type combined container-syringe, the third step may include: a filling step of filling an injection drug solution into each of the plurality of cartridges; a sealing step of sealing the injection drug solution along with an internal gas within the cartridge by the middle stopper and the front stopper; and a lyophilizing step of lyophilizing the injection drug solution to make the injection drug solution into a lyophilized preparation as the drug. Further, the lyophilizing step may include: a freezing process of freezing the injection drug solution; a pressure-reducing process of making the pressure of an external atmosphere lower than the pressure of the internal gas within the cartridge to bring the front stopper into a partially closed state with respect to the cartridge; a drying process of changing the injection drug solution to the lyophilized preparation due to a sublimation action; a replacement process of replacing the internal gas within the cartridge with pure nitrogen; and a sealing process of pushing the front stopper in the partially closed state into the cartridge.

According to the method for manufacturing a dual-chamber type combined container-syringe of such a feature, a pressure differential is caused between the external atmosphere and the internal gas by making the pressure of the external atmosphere lower than the internal gas between the middle stopper and the front stopper within the cartridge after the injection drug solution sealed within the cartridge is frozen. Then, as this pressure differential acts on the front stopper, the front stopper moves toward the tip end side of the cartridge, and as a result, the front stopper is brought into a partially closed state with respect to the cartridge. Thereby, since the inside and outside of the cartridge are brought into a communication state, the injection drug solution can be lyophilized by the cooled external atmosphere and the reduced pressure due to a sublimation action. Additionally, the lyophilized preparation in which the injection drug solution is lyophilized can be aseptically held in a sealed state within a lyophilizer by pushing the front stopper into the cartridge after the lyophilization is completed.

Additionally, in the first aspect related to the method for manufacturing a dual-chamber type combined container-syringe, between the second step and the third step, an autoclave sterilization step of exposing the plurality of cartridges to steam in a state where the plurality of cartridges is supported by the supporting plate via the plurality of holders may be performed.

Thereby, steam sterilization can be performed on the cartridge after the solvent is filled by the second step, and sterility can be further guaranteed.

Moreover, the first aspect related to the method for manufacturing a dual-chamber type combined container-syringe may further include, after the third step, a front assembly fitting step of removing the plurality of cartridges, to each of which a corresponding one of the plurality of holders is fitted, from the supporting plate, and externally fitting each of a plurality of front assemblies to a corresponding one of the plurality of cartridges while each of the plurality of holders is pressed downward by a corresponding one of the plurality of front assemblies.

Thereby, since the holder moves downward simultaneously when the hub lure lock is attached to the cartridge, the attachment of the hub lure lock to the cartridge can be smoothly performed.

Additionally, the first aspect related to the method for manufacturing a dual-chamber type combined container-syringe may further include, after the front assembly fitting step, a holder removing step of moving the plurality of holders downward relative to the plurality of cartridges to remove each of the plurality of holders from lower sides of the plurality of cartridges.

Thereby, the holder can be easily removed from below the cartridge without interfering with the front assembly.

According to the cartridge set for manufacturing a syringe and the method for manufacturing a dual-chamber type combined container-syringe of the present invention, since the cartridge along with the holder can move within the horizontal direction of the supporting plate within a range of the inner diameter of the through-hole, position adjustment of the cartridge can be easily performed. Accordingly, it is possible to mechanically execute operations, such as insertion of each of the front, middle, and end stoppers into the dual-chamber type combined container-syringe, or filling or sealing the solvent, the injection drug solution, or powder preparation easily and smoothly.

BRIEF DESCRIPTION OF THE DRAWINGS

FIG. 3A is a longitudinal sectional view illustrating a procedure of externally fitting a holder to a cartridge.

FIG. 3B is a longitudinal sectional view illustrating the procedure of externally fitting the holder to the cartridge.

FIG. 7A is a view illustrating an injection drug sealing step in a drug filling step related to the first embodiment.

FIG. 7B is a view illustrating the injection drug sealing step in the drug filling step related to the first embodiment.

FIG. 9A is a view illustrating a sealing process in the lyophilizing step of the drug filling step related to the first embodiment.

FIG. 9B is a view illustrating the sealing process in the lyophilizing step of the drug filling step related to the first embodiment.

FIG. 9C is a view illustrating the sealing process in the lyophilizing step of the drug filling step related to the first embodiment.

FIG. 10A is a view illustrating a front assembly fitting step related to the first embodiment.

FIG. 10B is a view illustrating the front assembly fitting step related to the first embodiment.

FIG. 11A is a view illustrating a holder removing step related to the first embodiment.

FIG. 11B is a view illustrating the holder removing step related to the first embodiment.

DETAILED DESCRIPTION OF THE INVENTION

Hereinafter, embodiments of the invention will be described in detail with reference to the drawings.

First, a dual-chamber type combined container-syringe (hereinafter simply referred to as "combined container-syringe") manufactured by a method for manufacturing a dual-chamber type combined container-syringe according to a first embodiment will be described with reference to FIG. 1.

Figure 1:
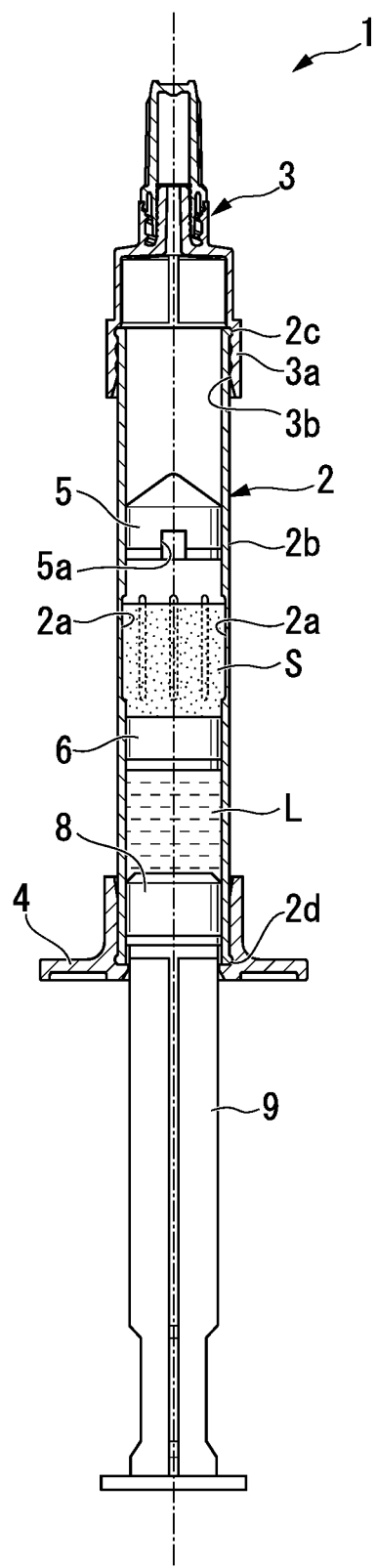
FIG. 1 is a schematic configuration view of a dual-chamber type combined container-syringe related to a first embodiment.

As shown in FIG. 1, a combined container-syringe 1 is equipped with a cartridge 2, a front assembly 3 that is attached to the tip end side (upper side in FIG. 1) of the cartridge 2, a finger grip 4 that is made of a synthetic resin and is fitted to the outer periphery of the cartridge 2 on the rear end side of the cartridge 2, stoppers of a front stopper 5, a middle stopper 6, and an end stopper 8 that are sequentially positioned in the cartridge 2 from the tip end side of the cartridge 2, and a rod-shaped plunger rod 9 that is connected to the end stopper 8 from the rear end side of the cartridge 2.

Lyophilized preparation (drug) S is filled between the front stopper 5 and the middle stopper 6, and a solvent L is filled between the middle stopper 6 and the end stopper 8. In addition, a bypass portion 2a is provided on the tip end side of the cartridge 2 in a place where the middle stopper 6 is positioned. The bypass portion 2a is formed so that a portion of an inner peripheral surface of the cartridge 2 is recessed radially outward and extends in the axis direction of the cartridge 2. On the other hand, an outer peripheral surface 2b of the cartridge 2 is adapted to have a uniform outer diameter. That is, the bypass portion 2a of the present embodiment is a so-called micro bypass formed within a range of the thickness of the cartridge 2 without protruding from the outer peripheral surface 2b.

Moreover, annular ribs (a tip-end-side annular rib 2c and a rear-end-side annular rib 2d) that overhang in the shape of a ring radially outward from the outer peripheral surface 2b are formed at both ends of the outer peripheral surface 2b, that is, the opening end portions of the cartridge 2.

The front assembly 3 has a hub lure lock 3a that is made of a transparent synthetic resin having moderate rigidity and forms a multi-stage columnar outer shape. The front assembly 3 and the cartridge 2 are firmly fixed and integrated by externally fitting a fitting hole 3b that is the inside of a base end portion of the hub lure lock 3a to the tip end of the cartridge 2.

Additionally, an air discharge groove 5a is formed by being cut out the front stopper 5 along the outer peripheral surface of the front stopper 5 from the face of the front stopper 5 that faces the middle stopper 6.

The lyophilized preparation S is prepared to powder by performing lyophilization processing on an injection drug solution (medicinal components) M, and the solvent L is used to dissolve or suspend the lyophilized preparation S to reconstitute the injection drug solution.

In the combined container-syringe 1, when the end stopper 8 is pushed toward the tip end side by the plunger rod 9, the solvent L filled between the end stopper 8 and the middle stopper 6 moves forward along with the end stopper 8 and the middle stopper 6. Then, when the middle stopper 6 reaches the bypass portion 2a in the cartridge 2, the sealing of the solvent L by the middle stopper 6 is released by the bypass portion 2a.

Thereby, the solvent L passes through the bypass portion 2a and flows into a portion where the lyophilized preparation S is filled, and the lyophilized preparation S is dissolved by the solvent L to prepare the injection drug to be injected to a patient. This brings about a state where the injection drug can be administered to a patient.

Next, a cartridge set 10 for manufacturing a syringe which is used when manufacturing the above combined container-syringe 1 will be described with reference to FIGS. 2, 3A, and 3B.

The cartridge set 10 for manufacturing a syringe is equipped with the above cartridges 2 arranged so as to extend in an up-and-down direction, holders 11, a supporting plate 20, a storage box 30, and a lid member 40.

Figure 2:
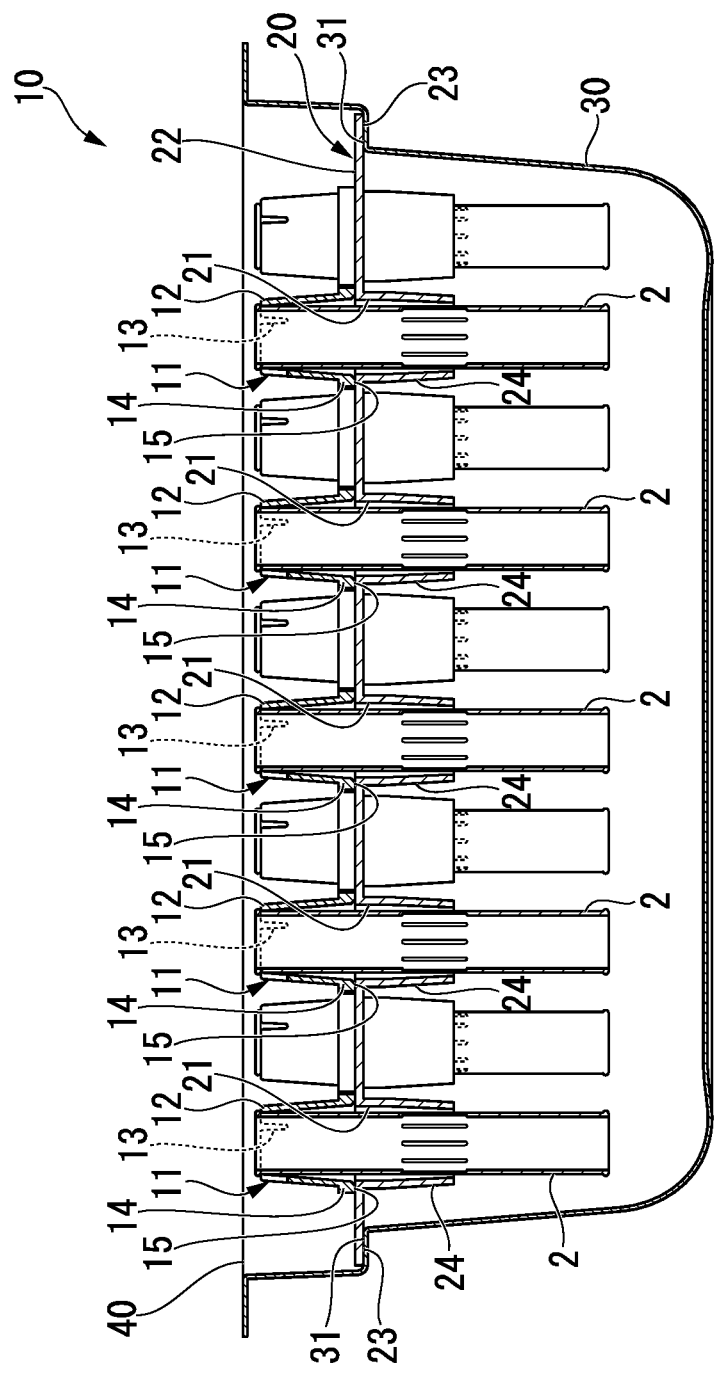
FIG. 2 is a longitudinal sectional view of a cartridge set for manufacturing a syringe related to the first embodiment.

As shown in FIGS. 2, 3A, and 3B, the holder 11 is coaxially and externally fitted to the cartridge 2. The holder 11 forms a tapered cylindrical shape whose diameter increases gradually as it goes downward from an upper portion of the cartridge 2 that extends in the up-and-down direction, that is, as it goes to the rear end side from the tip end side of the cartridge 2.

The holder 11 is molded from a resin material having flexibility, such as polycarbonate, and the inner diameter of an upper end portion 12 of the holder 11 is set to be equal to or slightly smaller than the outer diameter of the outer peripheral surface 2b of the cartridge 2. Thereby, the upper end portion 12 of the holder 11 abuts the outer peripheral surface 2b of the cartridge 2 by the restoring force of the holder 11 itself. In addition, the upper end portion 12 of the holder 11 abuts the tip-end-side annular rib 2c of the cartridge 2 extending in the up-and-down direction.

In this way, as the holder 11 abuts the cartridge 2 from the radial outside and from below, the holder 11 supports the cartridge 2 so that the cartridge 2 is hung.

A plurality of slits 13 that extend downward from the upper end portion 12 are formed at intervals in the circumferential direction in the holder 11. Thereby, the holder 11 is adapted such that the diameter of the upper end portion 12 thereof can be easily increased.

Moreover, a flange portion 14 that annularly overhangs radially outward is formed on the lower end side of the holder 11. The inner diameter of the flange portion 14 is set to be greater than, the outer diameter of the outer peripheral surface 2b, the tip-end-side annular rib 2c, and the rear-end-side annular rib 2d of the cartridge 2. Additionally, a lower face of the flange portion 14, that is, a lower end face 15 of the holder 11, is formed into a flat shape orthogonal to the axis of the cartridge 2 and an annular shape centering on the axis.

As shown in FIGS. 3A and 3B, the holder 11 is externally fitted to the cartridge 2 from above the cartridge 2 that has been subjected to a cleaning process and a silicon process. In this case, as the diameter on the upper end portion 12 side of the holder 11 is increased by the tip-end-side annular rib 2c, the holder 11 rides over the tip-end-side annular rib 2c. Note that, when the holder 11 is externally fitted to the cartridge 2 in this way, it is preferable to perform this fitting by applying a force to the flange portion 14 of the holder 11.

Thereafter, the upper end portion 12 of the holder 11 is restored, abuts the outer peripheral surface 2b of the cartridge 2, and abuts the tip-end-side annular rib 2c from below. Thereby, the holder 11 is held so as not to slip out of the cartridge 2 unless an external force is applied to the holder 11.

As shown in FIG. 2, the supporting plate 20 forms a plate shape that extends along the horizontal surface. A plurality of through-holes 21 that pass through the supporting plate 20 in the up-and-down direction are arranged and formed in the supporting plate 20. In the present embodiment, a number of through-holes 21 are formed at intervals in the horizontal direction so as to become staggered in plan view. The inner diameter of the through-hole 21 is set such that the cartridge 2 can be inserted through the through-hole 21, that is, is set to be greater than the outer diameter of the outer peripheral surface 2b, the tip-end-side annular rib 2c, and the rear-end-side annular rib 2d of the cartridge 2. Additionally, the inner diameter of the through-hole 21 is set to be smaller than the outer diameter of the lower end face 15 of the holder 11, and in the present embodiment, is set to be equal to or smaller than the inner diameter of the lower end face 15.

The face of the supporting plate 20 that faces upward is a top face 22 for placement that is parallel to the horizontal surface. The lower end face 15 of the holder 11 is placed on the top face 22. Additionally, the face of the supporting plate 20 that faces downward is parallel to the top face 22 for placement. The outer edge of the supporting plate 20, that is, the region on the outer peripheral side of the supporting plate 20 is a supported portion 23 which is supported by the storage box 30 from below.

A plurality of sleeves 24 are formed in the supporting plate 20 so as to correspond to the respective through-holes 21. The plurality of sleeves 24 are formed so that the edge portion of each through-hole 21 extends downward in a tubular shape. The inner diameter of the sleeve 24 forms a tapered shape whose diameter decreases gradually as it goes downward, and the inner diameter of the sleeve 24 at its lower end is set to be equal to or slightly greater than the outer diameter of the rear-end-side annular rib 2d of the cartridge 2. Thereby, the rear-end-side annular rib 2d of the cartridge 2 can pass through the lower end of the sleeve 24 when the cartridge 2 is inserted in the through-hole 21. In addition, the inner diameter of the upper end of the sleeve 24 is set to the same dimension as the inner diameter of the through-hole 21.

The cartridge 2 to which the holder 11 is externally fitted is inserted through each through-hole 21 of the supporting plate 20 from above. Then, as the lower end face 15 of the holder 11 is placed on the top face 22 for placement of the supporting plate 20 in a state where the cartridge 2 is inserted through the through-hole 21 in this way, the cartridge 2 is supported by the supporting plate 20 via the holder 11. In this case, the rear end of the cartridge 2 passes through the lower end of the sleeve 24 downward from above, and is located below the lower end of the sleeve 24. Additionally, the inner edge of the through-hole 21 faces the outer peripheral surface 2b of the cartridge 2 in the radial direction.

As the holder 11 is attached to the cartridge 2 in this way, the cartridge 2 can be packed in the storage box 30 as it is. Note that the material of the supporting plate 20 may be of any material type as long as they are heat-resistant and cold-resistant materials so that neither damage nor deformation is caused even if the materials are exposed to severe environmental conditions, such as being subjected to steam sterilization at a temperature of around 120° C. or being lyophilized in an ultralow temperature state, in a state where 50 to 100 cartridges 2 are hung. For example, the material of the supporting plate 20 may be polycarbonate; in terms of materials like plastics. Otherwise, a supporting plate 20 may be used as the supporting plate 20 for reuse by boring the same number of through-holes 21 as that of the supporting plate 20 made from plastics in a thin metal plate, such as stainless steel, so as to be slightly greater than those of the supporting plate 20 made from plastics, and fitting sleeves molded with the same inner diameter as the supporting plate 20 made from plastics into the through-holes 21.

The storage box 30 forms a rectangular box that opens upward and is molded from, for example, synthetic resins, such as plastics. Upper portions of four side walls of the storage box 30 are further increased in diameter toward the outside of the storage box 30. Thereby, a supporting portion 31 that forms a flat surface shape that faces upward is formed over the entire inner periphery of the storage box 30. The supported portion 23 of the supporting plate 20 abuts the supporting portion 31 from above in a state where the supporting plate 20 supports the cartridges 2 via the holders 11. Thereby, the supporting plate 20 is supported by the supporting portion 31 in a state where the supporting plate 20 is stored in the storage box 30.

The lid member 40 is a member that blocks the top opening of the storage box 30. Non-woven fabrics, such as Tyvek, which is welded to the outer periphery of the opening of the storage box 30 through heat sealing or the like, can be used as the lid member 40. Thereby, sterilization within the storage box 30 can be performed, and the sterility of the inside of the storage box 30 is guaranteed after the sterilization.

In the cartridge set 10 for manufacturing a syringe of such a configuration, the cartridge 2 is supported by the supporting plate 20 as the lower end face 15 of the holder 11 externally fitted to the outer peripheral surface 2b of the cartridge 2 is placed on the top face 22 for placement of the supporting plate 20. In this case, since the inner diameter of the through-hole 21 through which the cartridge 2 is inserted is formed so as to be greater than the outer diameter of the outer peripheral surface 2b of the cartridge 2, the cartridge 2 can be moved along with the holder 11 in the horizontal direction within a range of the inner diameter of the through-hole 21.

Figure 4:
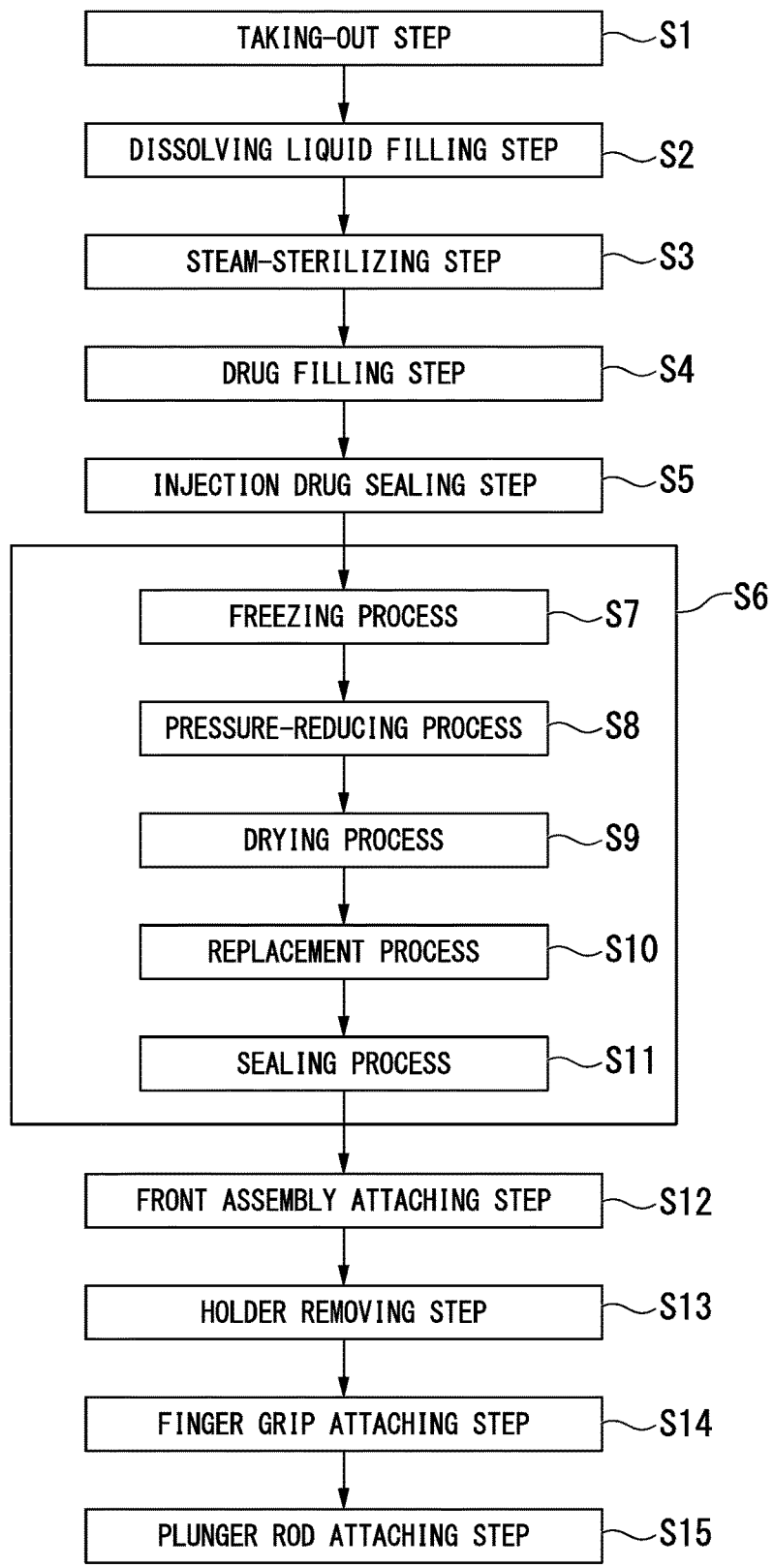
FIG. 4 is a flowchart of a method for manufacturing a dual-chamber type combined container-syringe related to the first embodiment.

Next, the method for manufacturing the combined container-syringe 1 using the cartridge set 10 for manufacturing a syringe of the above configuration will be described in order with reference to the flowchart of FIG. 4. After the cartridge set 10 for manufacturing a syringe described above is manufactured by a syringe maker, the cartridge set 10 is conveyed to a pharmaceutical maker, and the following steps are performed on the cartridge set 10 by the pharmaceutical maker.

This manufacturing method includes a taking-out step S1, a solvent filling step S2, an autoclave sterilization step S3, a drug filling step S4, an injection drug sealing step S5, a lyophilizing step S6, a front assembly fitting step S12, a holder removing step S13, a finger grip fitting step S14, and a plunger rod fitting step S15.

Figure 5:
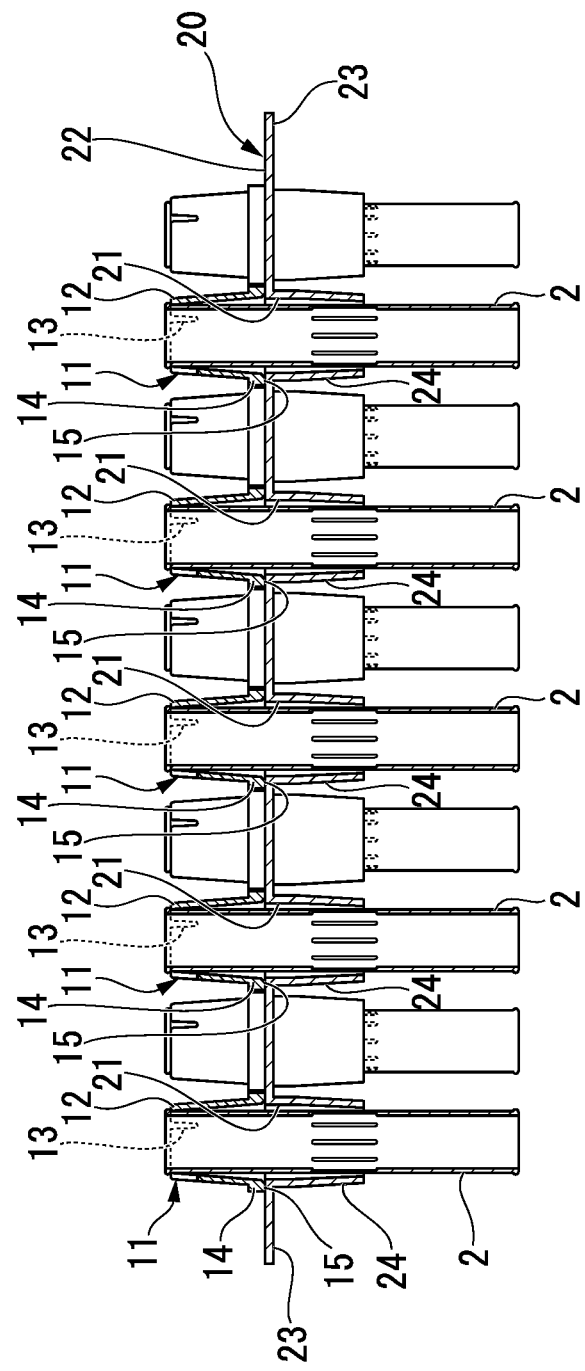
FIG. 5 is a view illustrating a taking-out step from a storage box related to the first embodiment.

In the taking-out step S1, the storage box 30 and the lid member 40, which are packing-material outer peripheral surfaces of the cartridge set 10 for manufacturing a syringe that is sterilized in advance, are sterilized, and then carried into the inside of a filling equipment, and the lid member 40 is peeled off. Thereafter, as shown in FIG. 5, the supporting plate 20 is taken out from the storage box 30 in a state where the cartridges 2 are supported by the supporting plate 20 via the holders 11. Then, the supporting plate 20, the holders 11, and the cartridges 2 are put on a holding table of a filling machine and are accurately positioned. Note that various filling operations are performed for every supporting plate 20.

Figure 6A:
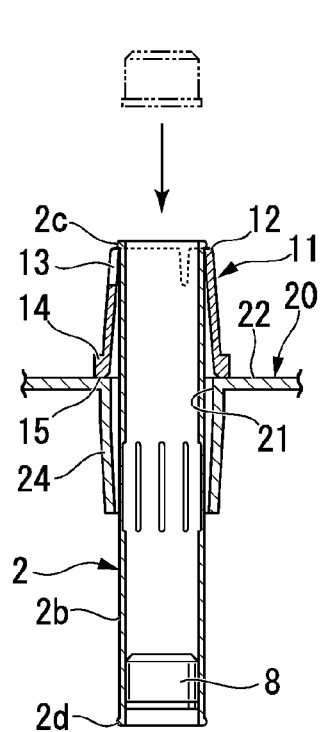
FIG. 6A is a view illustrating a solvent filling step related to the first embodiment.

Next, the solvent filling step S2 is performed. The solvent filling step S2 is performed by the filling machine. First, as shown in FIG. 6A, the end stopper 8 is inserted into the inside of each cartridge 2, which is supported by the supporting plate 20 via the holder 11, from above. Thereby, the end stopper 8 is inserted into the lower end side, that is, the rear end side of the cartridge 2.

Figure 6B:
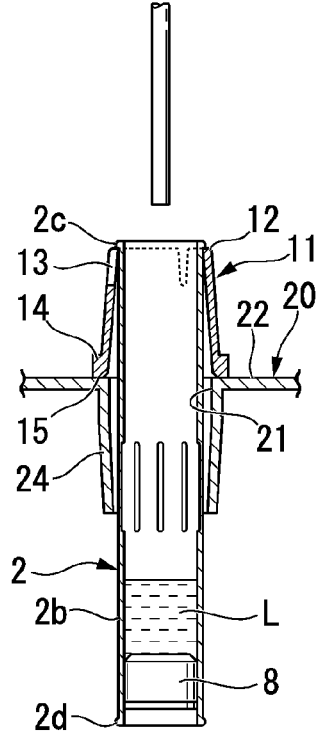
FIG. 6B is a view illustrating the solvent filling step related to the first embodiment.

Thereafter, as shown in FIG. 6B, a solvent L is filled into the inside of the cartridge 2 from above the cartridge 2. In this case, as the rear end side of the inside of the cartridge 2 is blocked by the end stopper 8, the solvent L is filled on the end stopper 8 inside the cartridge 2.

Subsequently, the middle stopper 6 is inserted from the upper end side, that is, the tip end side of the cartridge 2.

Figure 6C:
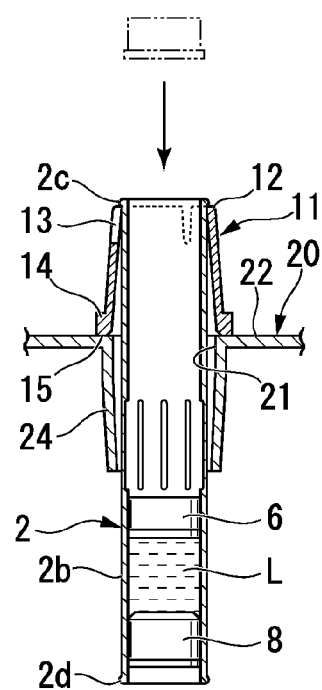
FIG. 6C is a view illustrating the solvent filling step related to the first embodiment.

Thereby, the middle stopper 6 is inserted into the cartridge 2 at a position below the bypass portion 2a, and as shown in FIG. 6C, the solvent L is sealed between the middle stopper 6 and the end stopper 8. This operation is performed by putting the middle stopper 6 at the position of the bypass portion 2a once, and then pushing in the middle stopper 6 while suctioning the air inside the cartridge 2, that is, while bringing the inside of the cartridge 2 into a vacuum state.

Thereby, entering of air between the middle stopper 6 and the end stopper 8 can be avoided, and only the solvent L can be sealed between the middle stopper 6 and the end stopper 8. That is, it is possible to avoid bubbles being mixed in the solvent L between the middle stopper 6 and the end stopper 8 by performing such bubble free filling.

Thereafter, the autoclave sterilization step S3 is performed on the cartridge 2 in which the solvent L has been sealed. The autoclave sterilization step S3 is performed by putting the cartridges 2 and the supporting plate 20 supporting the cartridges 2 into a sterile container and exposing them to a high-temperature and high-pressure steam atmosphere. Accordingly, sterilization of the cartridges 2 and the solvent L at this stage is performed in this manner.

Next, the drug filling step S4 and the injection drug sealing step S5 are performed by the same method as that when the solvent L is previously filled into the cartridge 2 in which the sterilized solvent L is sealed as described above.

In the drug filling step S4, as shown in FIG. 7A, first, the inside of the cartridge 2 is filled with an injection drug solution M from the upper end side of the cartridge 2. In this case, as the middle stopper 6 has been inserted into the inside of the cartridge 2, the injection drug solution M is filled on the middle stopper 6 inside the cartridge 2.

Subsequently, as shown in FIG. 7B, the front stopper 5 is inserted from the upper end side of the cartridge 2, and the injection drug solution M is sealed between the front stopper 5 and the middle stopper 6. In this case, the gas inside the filling device along with the injection drug solution M is sealed between the front stopper 5 and the middle stopper 6 of the cartridge 2, that is, the injection drug solution M and the internal air A are sealed within the cartridge 2. Thereby, the injection drug sealing step S5 is completed.

Subsequently, the lyophilizing step S6 is performed. This lyophilizing step S6 is performed after the cartridges 2, after the injection drug sealing step S5, which are supported by the supporting plate 20 via the holders 11, are put into a dedicated metallic rack and are introduced into a lyophilizer chamber. Within this lyophilizing rack (the dedicated metallic rack), a freezing process S7, a pressure-reducing process S8, a drying process S9, a replacement process S10, and a sealing process S11 are sequentially performed.

In the freezing process S7, the lowering of the temperature within the lyophilizer chamber, that is, cooling the external atmosphere and a rack, in which the cartridges 2 supported by the supporting plate 20 via the holders 11 are installed, is performed to freeze the injection drug M. In the freezing process S7, it is preferable to cool the temperature of the rack in which the cartridge 2 is installed and the external atmosphere from −40° C. to −50° C. Thereby, the solvent L and the injection drug solution M within the cartridge 2 are frozen.

Then, after the injection drug solution M filled into the cartridge 2 is frozen, the pressure-reducing process S8 of reducing the pressure of the lyophilizer chamber to lower the pressure of the external atmosphere is performed. In this case, the pressure of the external atmosphere is made significantly lower than the pressure of the internal gas A between the middle stopper 6 and the front stopper 5 within the cartridge 2. Thereby, the pressure differential between the internal gas A and the external atmosphere acts on the front stopper 5 inserted into the cartridge 2, that is, as shown in FIG. 8A, the pressure P toward the tip end side (upper side) of the cartridge 2 acts on the front stopper 5.

As the pressure P acts on the front stopper 5 in this way, the front stopper 5 moves upward, that is, toward the tip end side of the cartridge 2. Then, when the front stopper 5 reaches the tip of the cartridge 2, as the front stopper 5 is brought into a partially closed state with respect to the cartridge 2, the pressures inside and outside the cartridge 2 are brought into an equilibrium state. That is, the inside and outside of the cartridge 2 are brought into a communication state via the air discharge groove 5a in the front stopper 5. Thereby, since the pressure P that has acted on the front stopper 5 disappears, movement of the front stopper 5 stops at the tip of the cartridge 2.

Figures 8A, 8B, 8C:
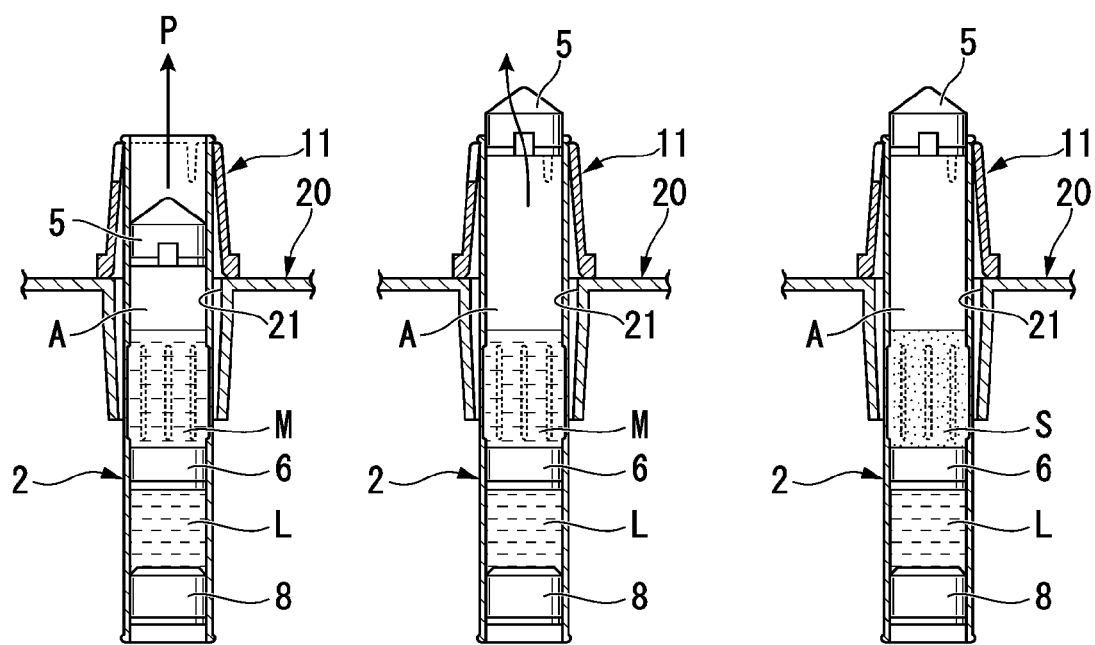
FIG. 8A is a view illustrating a pressure-reducing process in a lyophilizing step of the drug filling step related to the first embodiment.
FIG. 8B is a view illustrating the pressure-reducing process in the lyophilizing step of the drug filling step related to the first embodiment.
FIG. 8C is a view illustrating the pressure-reducing process in the lyophilizing step of the drug filling step related to the first embodiment.

Then, as shown in FIG. 8B, the moisture of the injection drug solution M is emitted to the outside via the upper end of the cartridge 2, which has been brought into a partially closed state, due to a sublimation action. When the cartridge 2 is left in this state for a while, lyophilization of the injection drug solution M proceeds, and as shown in FIG. 8C, the injection drug solution M changes to the lyophilized preparation S due to the sublimation action (the drying processing S9).

Thereafter, the inside of the lyophilizer chamber is replaced with a predetermined level of pure nitrogen gas (the replacement process S10). Thereby, the moisture within the lyophilizer chamber is removed, and in the space A within the cartridge 2, depending on the filling amount of the pure nitrogen, the descent position of the front stopper 5 is determined and the space between the front stopper and the lyophilized preparation is determined.

Subsequently, the sealing process S11 is performed. Here, as shown in FIG. 9A, a rack plate 50 installed above the cartridge 2 in the lyophilizer chamber is moved downward while being maintained in a horizontal state. Thereby, the rack plate 50 is made to abut the front stoppers 5 in the plurality of cartridges 2, respectively, and the front stoppers 5 are pushed into the cartridges 2. Then, the front stopper 5 pushed into the cartridge 2 in this way, as shown in FIG. 9B, moves downward due to the pressure differential between the inside and outside of the cartridge 2, and as shown in FIG. 9C, is finally located in a place that is suitable as the arrangement place of the front stopper 5 according to the amount of injected nitrogen gas.

Next, the front assembly fitting step S12 is performed. In the steps after this step, the cartridges 2 are removed from the supporting plate 20, and following steps are performed on each cartridge 2 separately from the supporting plate 20.

In the front assembly fitting step S12, the cartridge 2 to which the holder 11 is externally fitted is taken out from the supporting plate 20, as shown in FIG. 10A, the lower end, that is, the rear end of the cartridge 2 is placed on a horizontal table, and an intermediate portion of the cartridge 2 is supported by a presser member 51. This prevents toppling of the cartridge 2.

Then, the front assembly 3 is moved with respect to the cartridge 2 from above the cartridge 2 by a moving mechanism 52, and the fitting hole 3b of the hub lure lock 3a of the front assembly 3 is fitted to the upper end side of the cartridge 2. In this case, as shown in FIG. 10B, the front assembly 3 is externally fitted to the cartridge 2 while the holder 11 is pressed downward by the front assembly 3.

Next, the holder removing step S13 is performed. In the holder removing step S13, as shown in FIG. 11A, the front assembly 3 fitted to the cartridge 2 in the front assembly fitting step S12 is supported so as to hang from below the front assembly by a hanging supporting portion 53. Then, in this state, the holder 11 is moved downward by a holder moving portion 54. Thereby, the holder 11 rides over the rear-end-side annular rib 2d as the upper end portion 12 is increased in diameter by the rear-end-side annular rib 2d of the cartridge 2, and as shown in FIG. 11B, moves toward the lower side of the cartridge 2, that is, the holder 11 is removed from the outer peripheral surface 2b of the cartridge 2.

Thereafter, the finger grip 4 is fitted to the rear end side of the cartridge 2 (the finger grip fitting step S14), and the plunger rod 9 is connected to the end stopper 8 from the rear end side of the cartridge 2 (the plunger rod connecting step S15). From the above steps, the combined container-syringe 1 shown in FIG. 1 is completed.

According to the method for manufacturing the combined container-syringe 1 using the cartridge set 10 for manufacturing a syringe described above, the inner diameter of the through-hole 21 through which the cartridge 2 is inserted is formed to be greater than the outer diameter of the outer peripheral surface 2b of the cartridge 2. Accordingly, the cartridge 2 can move in the horizontal direction within a range of the inner diameter of the through-hole 21 along with the holder 11. That is, the cartridge 2 is supported by the supporting plate 20 with an allowance therebetween. Accordingly, position adjustment of the cartridge 2 with respect to the filling machine in the solvent filling step S2 and the drug filling step S4 can be easily and smoothly performed. This enables the combined container-syringe to be easily and smoothly manufactured.

Moreover, by using the holder 11, it is possible to safely perform the difficult operations, such as the filling and sealing of the solvent L, sterilization and drying of the solvent L after filling, the filling and sealing of the lyophilized preparation S, and aseptic manipulation of the fitting of the front assembly 3 on the cartridge 2 of the dual-chamber type combined container-syringe 1. Further, it is possible to perform the above difficult operations by mainly utilizing existing facilities.

Additionally, since the slits 13 are formed in the holder 11, the diameter of the holder 11 can be easily increased. This enables the holder 11 to be easily externally fitted to the cartridge 2 from above the cartridge. Additionally, when the combined container-syringe 1 is finally assembled, it is possible to easily remove the holder 11 from the lower end side of the cartridge 2.

Moreover, in the drug filling step S4 of the present embodiment, the pressure of the external atmosphere is made lower than the internal gas between the middle stopper 6 and the front stopper 5 within the cartridge 2 after the injection drug solution sealed within the cartridge 2 is frozen. This causes a pressure differential between the external atmosphere and the internal gas. Then, as this pressure differential acts on the front stopper 5, the front stopper 5 moves toward the tip end side of the cartridge 2, and as a result, the front stopper 5 is brought into a partially closed state with respect to the cartridge 2. Thereby, since the inside and outside of the cartridge 2 are brought into a communication state, the injection drug solution can be lyophilized by the cooled external atmosphere and the reduced pressure. Additionally, after the lyophilization is completed, the lyophilized preparation which is formed by lyophilizing the injection drug solution can be held in a sealed state by pushing the front stopper 5 into the cartridge 2.

Additionally, in the present embodiment, the front assembly 3 and the finger grip 4 are not fitted to the cartridge 2 when the lyophilizing step S6 is performed. Accordingly, it is possible to avoid that the resin front assembly 3 and the resin finger grip 4 deteriorate due to the lyophilization.

Moreover, the cartridge 2 can be densely arranged by such an amount that the front assembly 3 and the finger grip 4 are not attached. Accordingly, the efficiency of the lyophilization that requires a long amount of time can be remarkably enhanced, and the production efficiency of the combined container-syringe 1 can be improved.

Additionally, in the front assembly fitting step S12, the holder 11 moves downward by pressing the holder 11 by the front assembly 3 when the front assembly 3 is fitted to the cartridge 2. Accordingly, the sterility of the tip end portion of the cartridge 2 can be quickly held by the front assembly, and the attachment of the front assembly 3 to the cartridge 2 can be smoothly performed. That is, since the holder 11 does not hinder the attachment of the front assembly, the attachment can be smoothly performed.

Moreover, the holder 11 can be removed from below the cartridge 2 by moving the holder 11 downward relative to the cartridge 2. Accordingly, the holder 11 can be easily removed from below the cartridge 2 without interfering with the front assembly 3 that is already mounted.

Figure 12A:
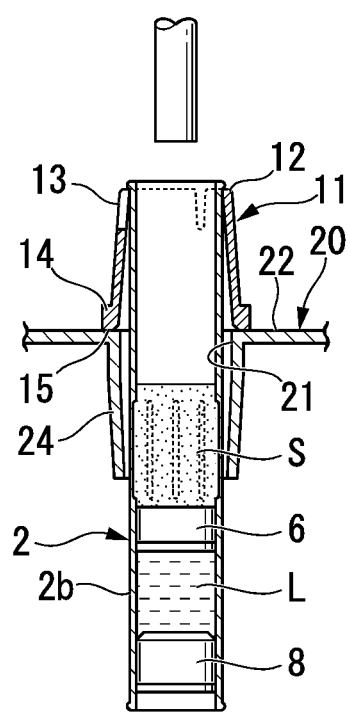
FIG. 12A is a view illustrating another example of powder filling related to the first embodiment.
Figure 12B:
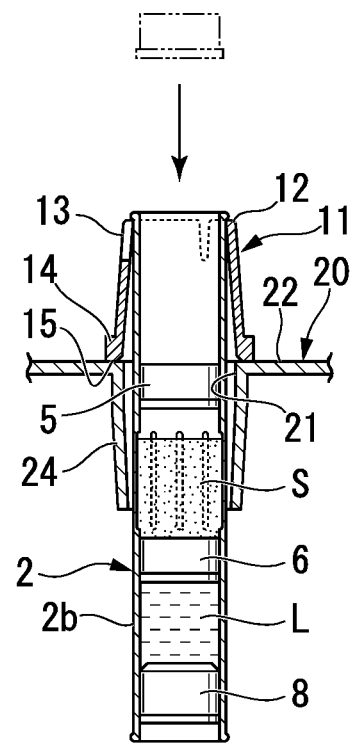
FIG. 12B is a view illustrating still another example of the powder filling related to the first embodiment.

Note that in the first embodiment, the example in which the injection drug solution sealed into the cartridge 2 in the injection drug sealing step S5 after the drug filling step S4 is made into a lyophilized preparation by the lyophilizing step S6 has been described. However, for example, a step of, as shown in FIG. 12A, filling the upper portion of the middle stopper 6 with a powdered drug from the upper end of the cartridge 2, and then, as shown in FIG. 12B, inserting the front stopper 5 into the cartridge 2 to seal the drug may be adopted.

Next, a second embodiment will be described. In the second embodiment, the same constituent elements as those of the first embodiment are designated by the same reference numerals, and detailed description thereof is omitted. A combined container-syringe 101 of the second embodiment is different from the first embodiment as for the shape of a bypass portion 102a of a cartridge 102, and the other configurations are the same as that of the first embodiment.

Figure 13:
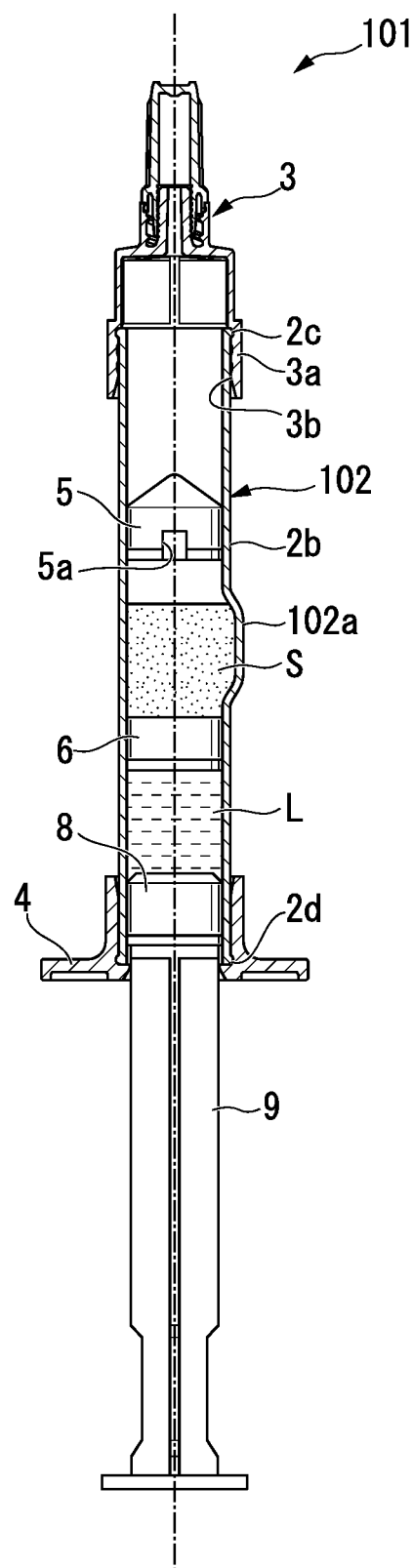
FIG. 13 is a schematic configuration view of a dual-chamber type combined container-syringe related to a second embodiment.

That is, as shown in FIG. 13, in the bypass portion 102a of the combined container-syringe 101 of the second embodiment, a portion of the inner peripheral surface of the cartridge 102 is recessed radially outward, and the outer peripheral surface 2b bulges radially outward so as to correspond to this. Thereby, the outer peripheral surface 2b does not have a uniform outer diameter, and protrudes radially outward in a portion where the bypass portion 102a is formed.

Figure 14:
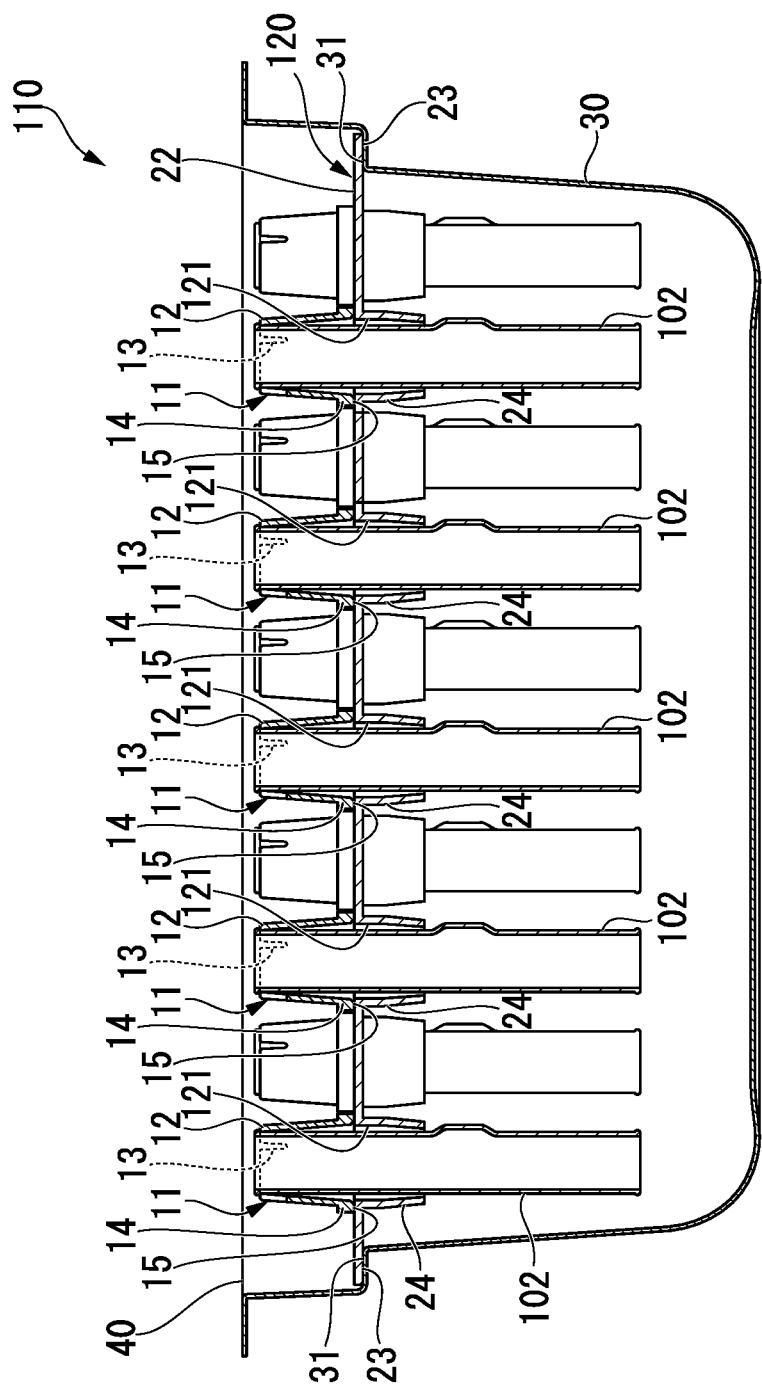
FIG. 14 is a longitudinal sectional view of a cartridge set for manufacturing a syringe related to the second embodiment.
Figure 15A:
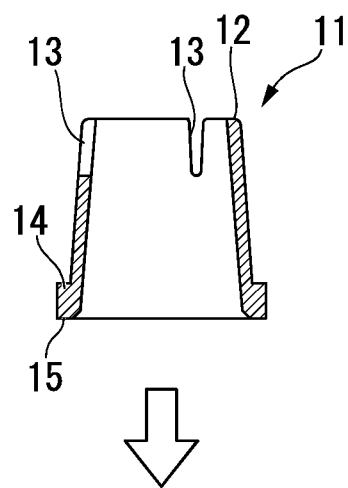
FIG. 15A is a longitudinal sectional view illustrating a procedure of externally fitting a holder to a cartridge.
Figure 15B:
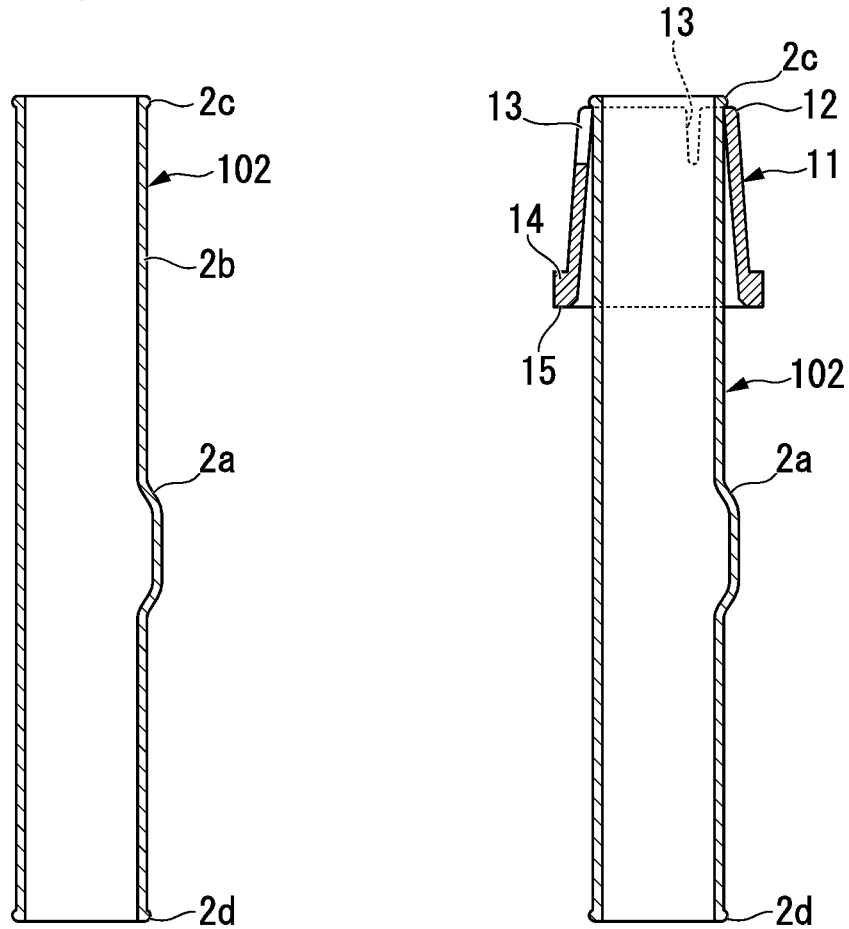
FIG. 15B is a longitudinal sectional view illustrating the procedure of externally fitting the holder to the cartridge.

Next, a cartridge set 110 for manufacturing a syringe used when manufacturing the above combined container-syringe 101 will be described with reference to FIGS. 14, 15A and 15B.

The cartridge set 110 for manufacturing a syringe is equipped with the above cartridges 102 arranged so as to extend in the up-and-down direction, the holders 11, a supporting plate 120, the storage box 30, and the lid member 40.

Figure 16:
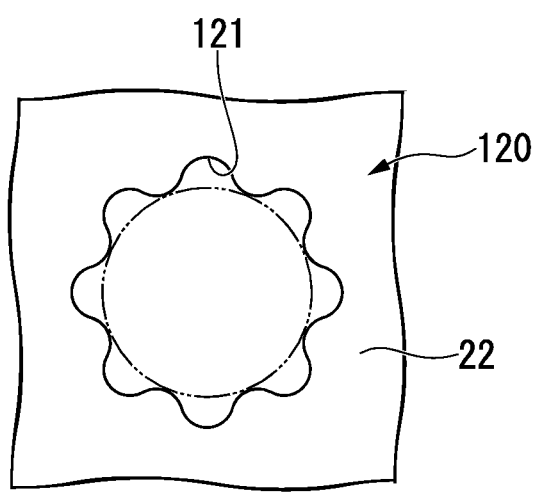
FIG. 16 is a plan view showing the shape of through-holes.

The supporting plate 120 of the present embodiment is different from the first embodiment only in the shape of through-holes 121 of the supporting plate 120. That is, as shown in FIG. 16, the shape of the through-hole 121 is formed into such a shape that the inner edge of the through-hole 121 is cut out in a shape corresponding to the bypass portion 102a so that the bypass portion 102a of the cartridge 102 can pass through the through-hole 121. In the present embodiment, a plurality of cutouts are formed in the circumferential direction so that the bypass portion 102a can pass through the through-hole 121 irrespective of the circumferential position thereof.

Figure 17:
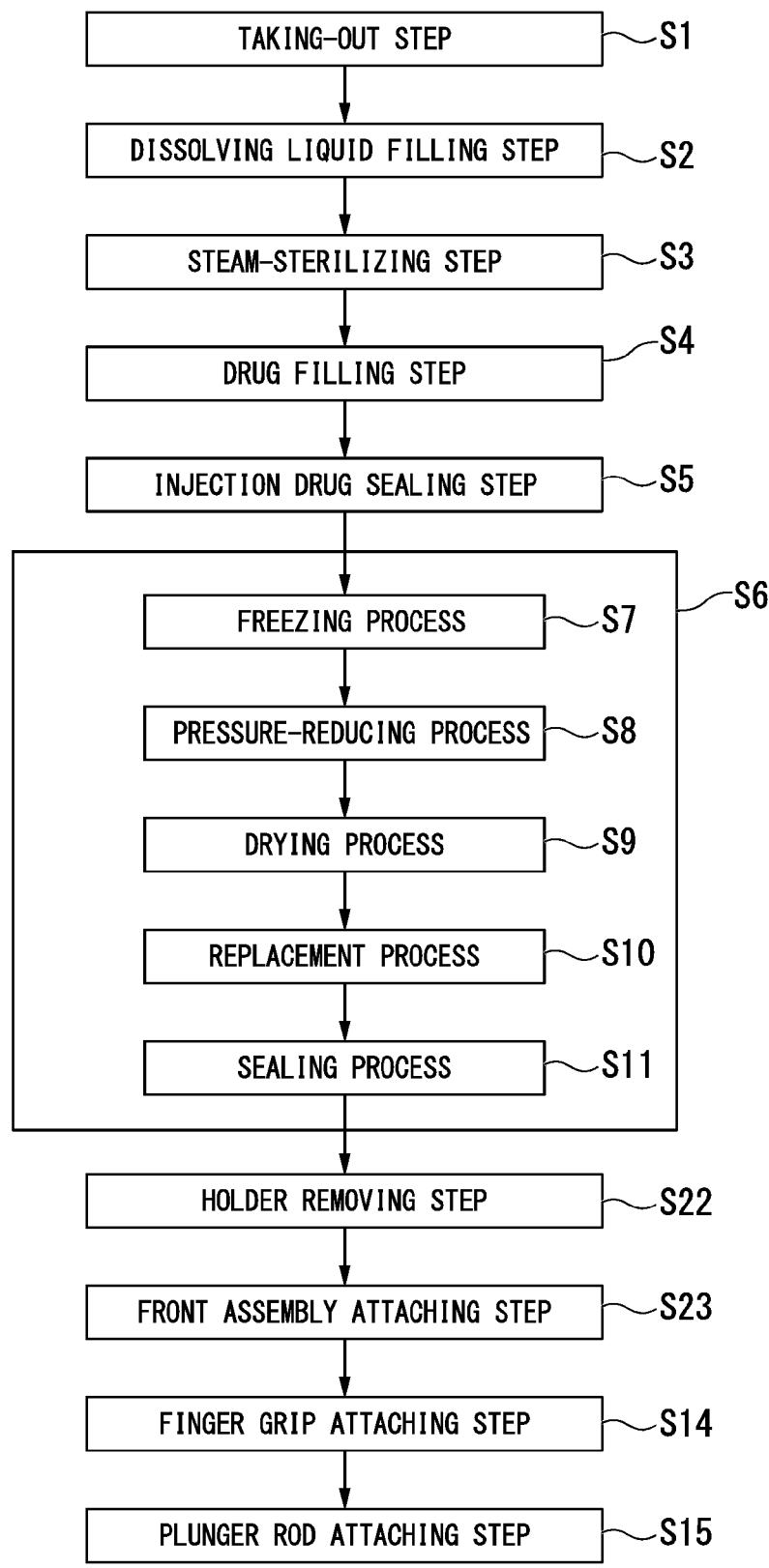
FIG. 17 is a flowchart of a method for manufacturing a dual-chamber type combined container-syringe related to the second embodiment.

Next, the method for manufacturing the combined container-syringe 101 using the cartridge set 110 for manufacturing a syringe of the above configuration will be described in order with reference to the flowchart of FIG. 17.

This manufacturing method includes the taking-out step S1, the solvent filling step S2, the autoclave sterilization step S3, the drug filling step S4, a holder removing step S22, a front assembly fitting step S23, the finger grip fitting step S14, and the plunger rod fitting step S15.

Figure 18:
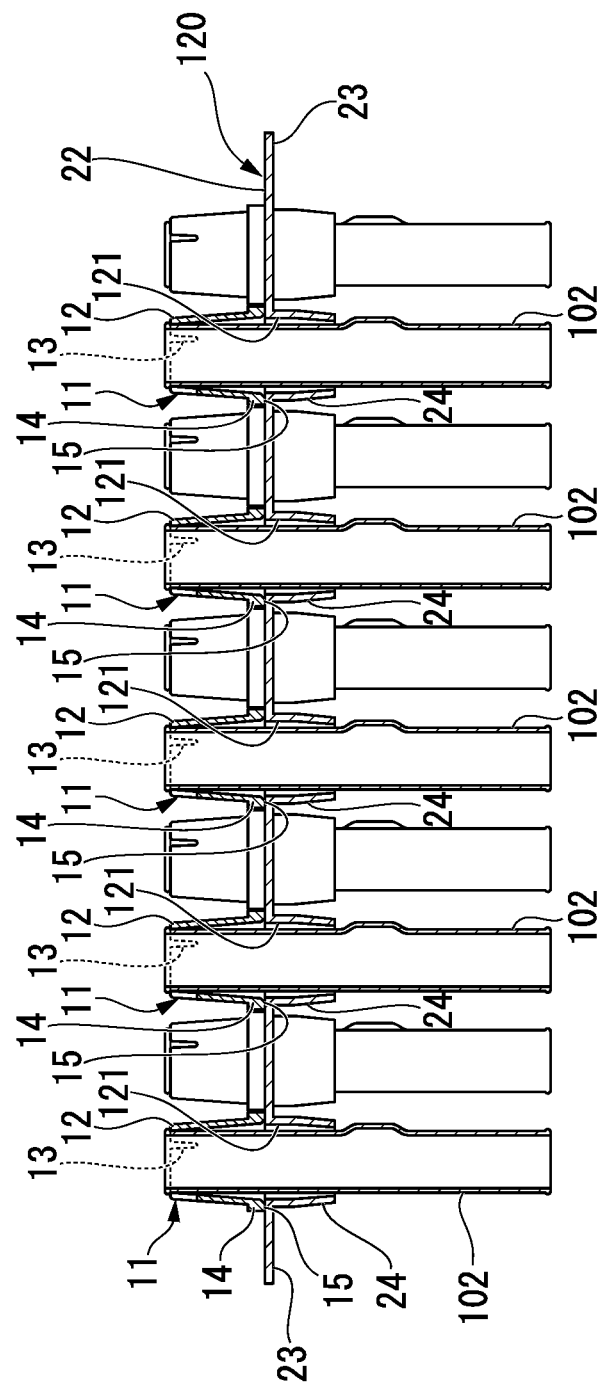
FIG. 18 is a view illustrating a taking-out step from a storage box related to the second embodiment.

As shown in FIG. 18, the taking-out step S1, similarly to the first embodiment, is a step of taking out the supporting plate 120 from the storage box 30 in a state where the cartridges 102 are supported by the supporting plate 120 via the holders 11.

Figures 19A, 19B, 19C:
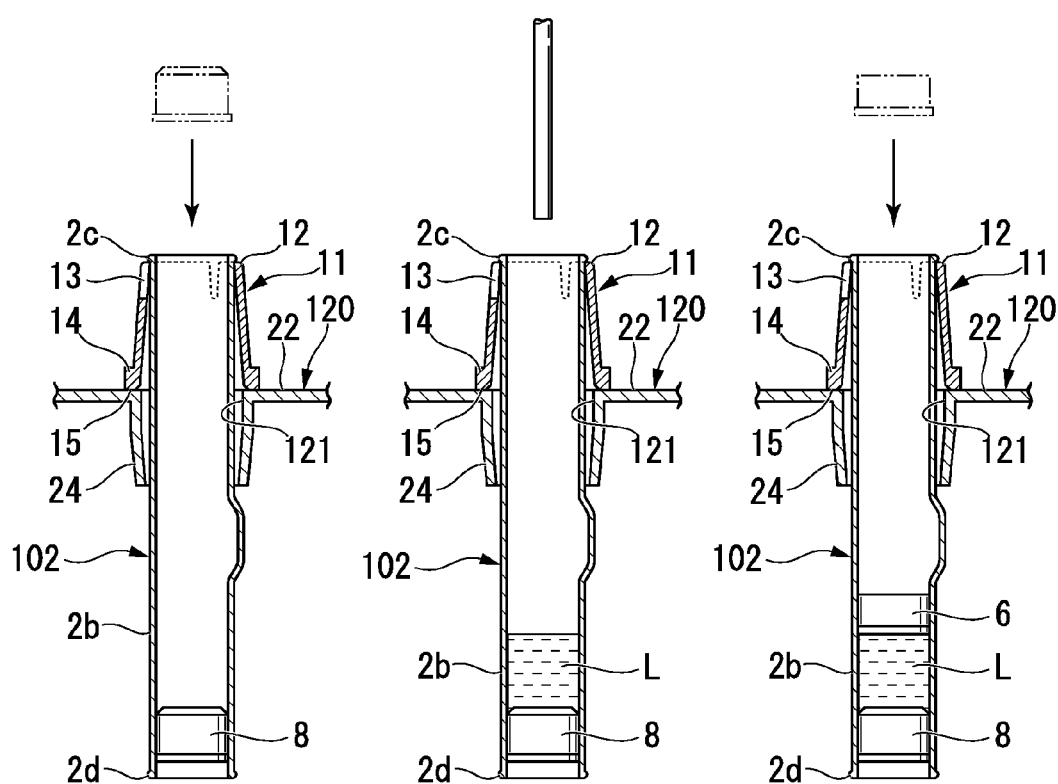
FIG. 19A is a view illustrating a solvent filling step related to the second embodiment.
FIG. 19B is a view illustrating the solvent filling step related to the second embodiment.
FIG. 19C is a view illustrating the solvent filling step related to the second embodiment.

As shown in FIGS. 19A to 19C, the solvent filling step S2, similarly to the first embodiment, is a step of inserting or filling the end stopper 8, the solvent L, and the middle stopper 6 into the cartridge 102.

The autoclave sterilization step S3, similarly to the first embodiment, is performed by putting the cartridges 102 and the supporting plate 120 supporting the cartridges 102 into a sterile container and exposing them to a high-temperature and high-pressure steam atmosphere.

The injection drug sealing step S5, similarly to the first embodiment, is performed after the drug filling step S4.

Figure 20A:
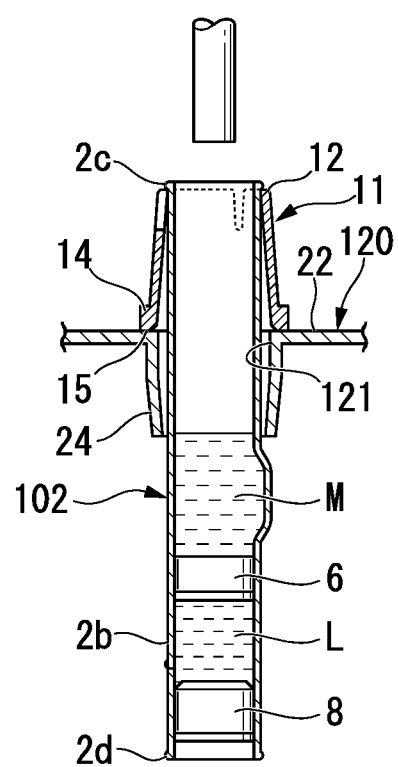
FIG. 20A is a view illustrating an injection drug sealing step in a drug filling step related to the second embodiment.
Figure 20B:
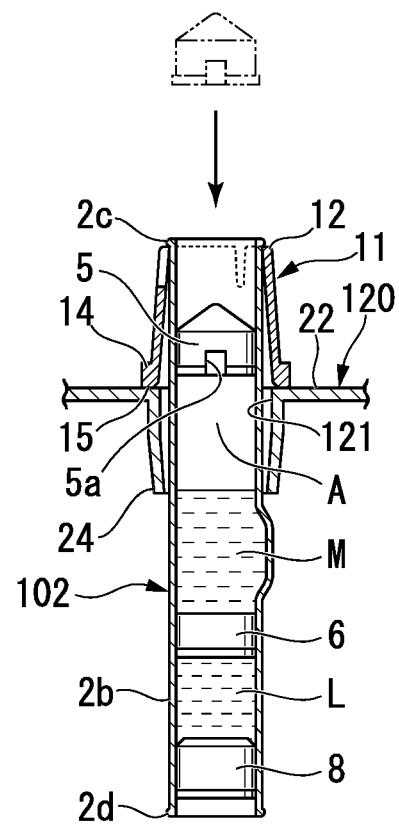
FIG. 20B is a view illustrating the injection drug sealing step in the drug filling step related to the second embodiment.

In the injection drug sealing step S5, similarly to the first embodiment, as shown in FIG. 20A, first, the inside of the cartridge 102 is filled with the injection drug solution M from the upper end side of the cartridge 102. Thereafter, as shown in FIG. 20B, the front stopper 5 is inserted from the upper end side of the cartridge 102.

The lyophilizing step S6 is performed within the lyophilizing rack, and similarly to the first embodiment, the freezing process S7, the pressure-reducing process S8, the drying process S9, the replacement process S10, and the sealing process S11 are sequentially performed.

In the freezing process S7, the temperature of the lyophilizer chamber is cooled from −40° C. to −50° C. similarly to the first embodiment. Thereby, the solvent L and the injection drug solution M within the cartridge 102 are frozen.

Figures 21A, 21B, 21C:
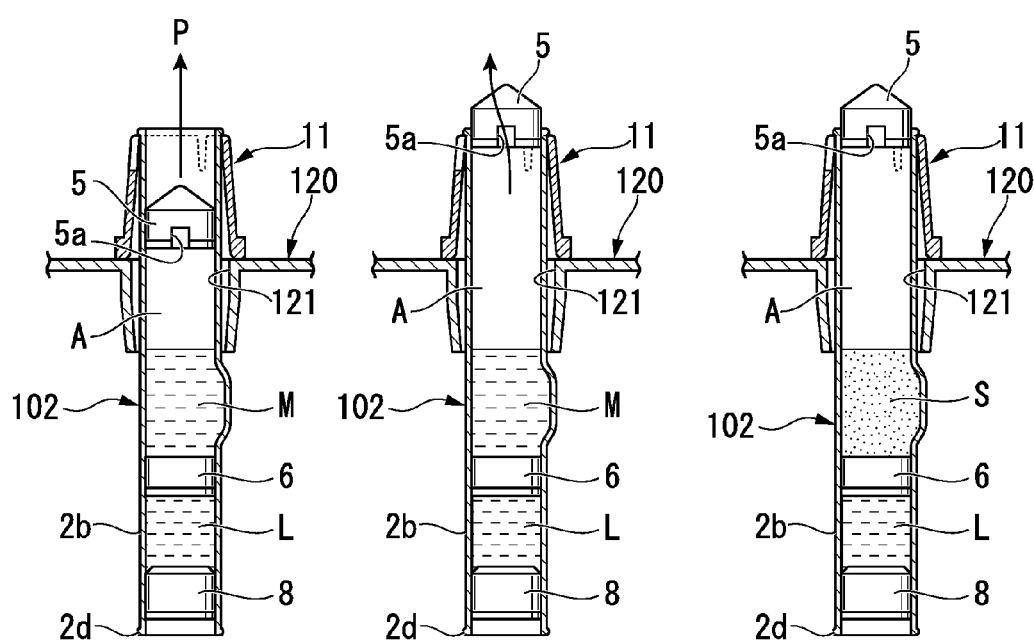
FIG. 21A is a view illustrating a pressure-reducing process in a lyophilizing step of the drug filling step related to the second embodiment.
FIG. 21B is a view illustrating the pressure-reducing process in the lyophilizing step of the drug filling step related to the second embodiment.
FIG. 21C is a view illustrating the pressure-reducing process in the lyophilizing step of the drug filling step related to the second embodiment.

Then, the pressure-reducing process S8 of reducing the pressure of the lyophilizer chamber to lower the pressure of the external atmosphere is performed. In this case, the pressure of the external atmosphere is made significantly lower than the pressure of the internal gas A between the middle stopper 6 and the front stopper 5 within the cartridge 102. Thereby, the pressure differential between the internal gas A and the external atmosphere acts on the front stopper 5 inserted into the cartridge 102, that is, as shown in FIG. 21A, the pressure P toward the tip end side (upper side) of the cartridge 102 acts on the front stopper 5.

As the pressure P acts on the front stopper 5 in this way, the front stopper 5 moves upward, that is, toward the tip end side of the cartridge 102. Then, when the front stopper 5 reaches the tip of the cartridge 102, the front stopper 5 is brought into a partially closed state with respect to the cartridge 102, and consequently, the pressures inside and outside the cartridge 102 are brought into an equilibrium state. That is, the inside and outside of the cartridge 102 are brought into a communication state via the air discharge groove 5a in the front stopper 5. Then, as shown in FIG. 21B, the moisture of the injection drug solution M is emitted to the outside via the upper end of the cartridge 102 that is brought into the partially closed state due to a sublimation action. Then, when the cartridge is left in this state for a while, drying of the injection drug M proceeds, and, as shown in FIG. 21C, the injection drug solution M changes to the lyophilized preparation S due to the sublimation action (the drying process S9).

Thereafter, the inside of the lyophilizer chamber is replaced with a predetermined level of pure nitrogen gas (the replacement process S10).

Figures 22A, 22B, 22C:
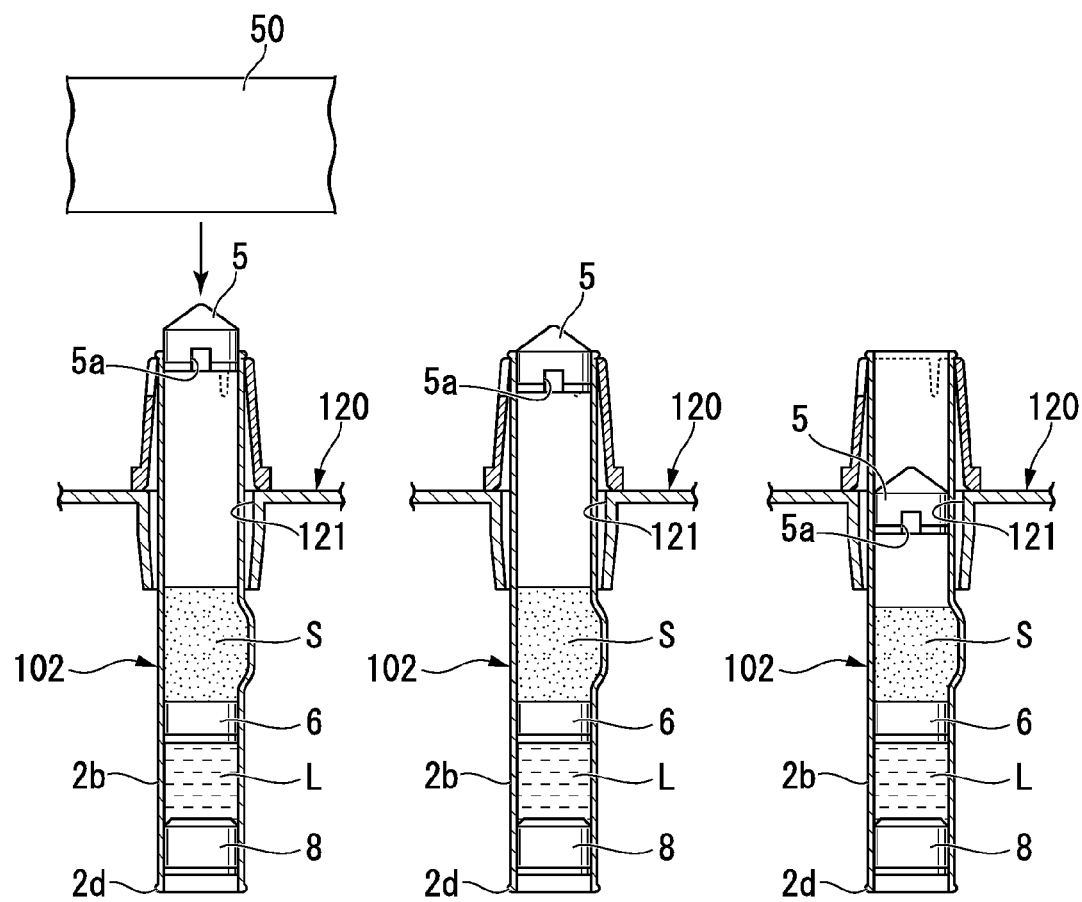
FIG. 22A is a view illustrating a sealing process in the lyophilizing step of the drug filling step related to the second embodiment.
FIG. 22B is a view illustrating the sealing process in the lyophilizing step of the drug filling step related to the second embodiment.
FIG. 22C is a view illustrating the sealing process in the lyophilizing step of the drug filling step related to the second embodiment.

Subsequently, the sealing process S11 is performed. Here, as shown in FIG. 22A, the rack plate 50 installed above the cartridge 102 in the lyophilizer chamber is moved downward while being maintained in a horizontal state. Thereby, the front stopper 5, as shown in FIG. 22B, moves downward due to the pressure differential between the inside and outside of the cartridge 102, and as shown in FIG. 22C, is finally located in a place that is suitable as the arrangement place of the front stopper 5 according to the amount of injected nitrogen gas.

Figure 23:
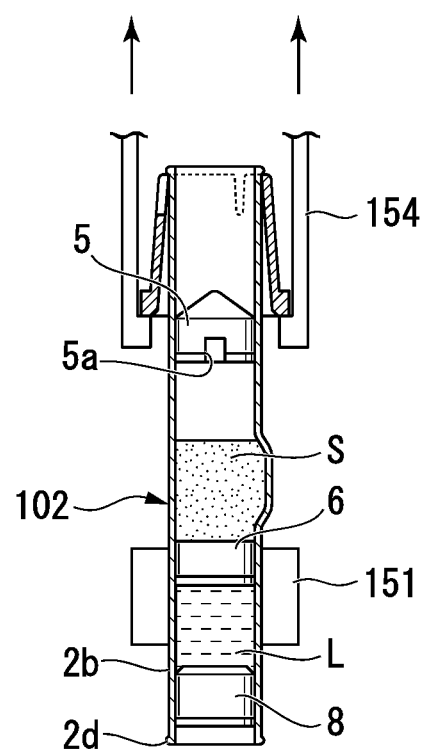
FIG. 23 is a view illustrating a holder removing step related to the second embodiment.

Next, the holder removing step S22 is performed. In the steps after this step, the cartridges 102 are removed from the supporting plate 120, and following steps are performed on each cartridge 102 separately from the supporting plate 120. In the holder removing step S22, as shown in FIG. 23, the holder 11 is moved upward by a holder moving portion 154 in a state where the outer peripheral surface of the cartridge 102 is pressed down by a presser member 151. Thereby, the holder 11 is removed from the outer peripheral surface 2b of the cartridge 102.

Next, the front assembly fitting step S23 is performed. In the front assembly fitting step S23, the lower end, that is, rear end of the cartridge 102 is placed on a horizontal table, and an intermediate portion of the cartridge 102 is supported by the presser member 151. This prevents toppling of the cartridge 102.

Figure 24:
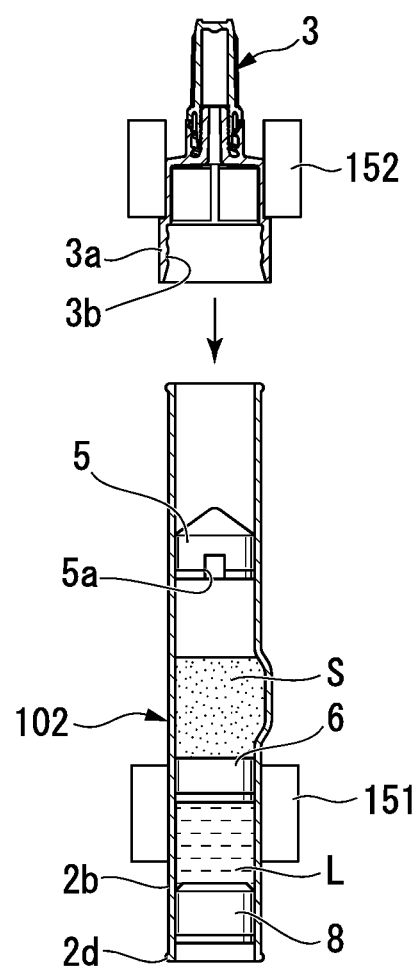
FIG. 24 is a view illustrating a front assembly fitting step related to the second embodiment.

Then, as shown in FIG. 24, the front assembly 3 is moved with respect to the cartridge 102 from above the cartridge 102 by a moving mechanism 152, and the fitting hole 3b of the hub lure lock 3a in the front assembly 3 is fitted to the upper end side of the cartridge 102.

Thereafter, the finger grip 4 is fitted to the rear end side of the cartridge 102 (the finger grip fitting step S14), and the plunger rod 9 is connected to the end stopper 8 from the rear end side of the cartridge 102 (the plunger rod connecting step S15). From the above steps, the combined container-syringe 101 shown in FIG. 13 is completed.

According to the method for manufacturing the combined container-syringes 101 as described above, similarly to the first embodiment, the cartridge 102 can move in the horizontal direction within a range of the inner diameter of the through-hole 121 along with the holder 111. This enables the dual-chamber type combined container-syringe to be easily and smoothly manufactured.

Although the embodiments of the invention have been described in detail, the invention is not limited to this unless departing from the technical scope of the invention, and some design changes or the like can also be made.

Figure 25:
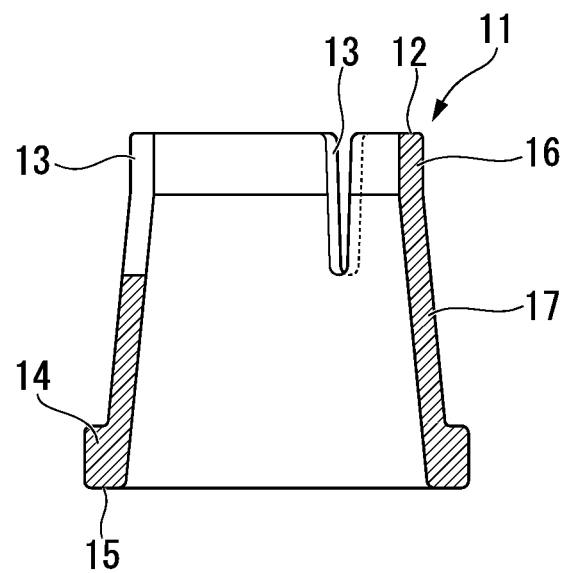
FIG. 25 is a longitudinal sectional view of a holder of an alternative example.

For example, a configuration shown in FIG. 25 may be adopted as a modification of the holder 11. The holder of this modification has a cylindrical body 16 having an inner peripheral surface capable of being brought into close contact with the outer peripheral surface 2b of the cartridge 2 at an upper portion of a tapered cylindrical portion of the holder 11. That is, the holder 11 has a structure in which the cylindrical body 16 is integrally formed on a tapered cylindrical body 17. Thereby, since the cylindrical body 16 coaxially comes into close contact with the outer peripheral surface 2b of the cartridge 2, the central axes of the holder 11 and the cartridge 2 can be certainly be made to coincide with each other.

Figure 26:
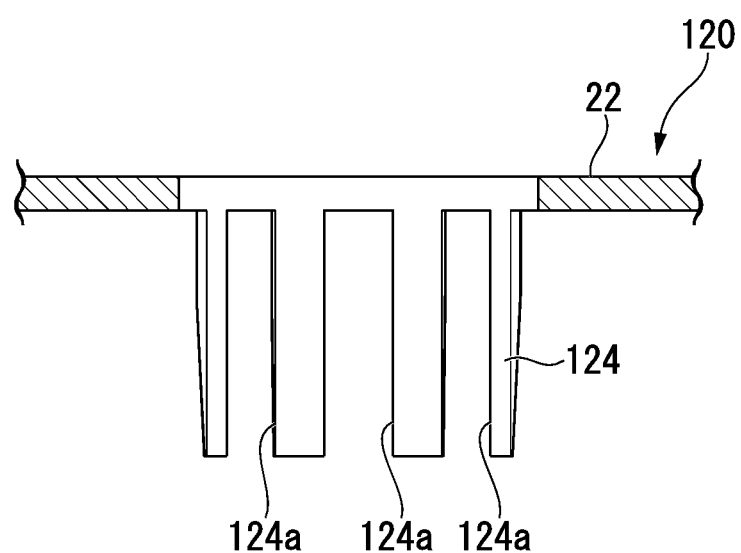
FIG. 26 is a longitudinal sectional view of sleeves of an alternative example.

Additionally, a sleeve 124 having a shape as shown in FIG. 26 may be adopted as a modification of the supporting plate 120 of the second embodiment.

Slits 124a are formed in the sleeve 124 according to the shape of the inner edge of the through-hole 121. That is, in the sleeve 124, the slits 124a are formed in the up-and-down direction in portions that correspond to the cutouts of the through-hole 121. Thereby, the cartridge 102 having the bypass portion 102a that bulges radially outward can be more smoothly inserted through the sleeve 124.

Figure 27A:
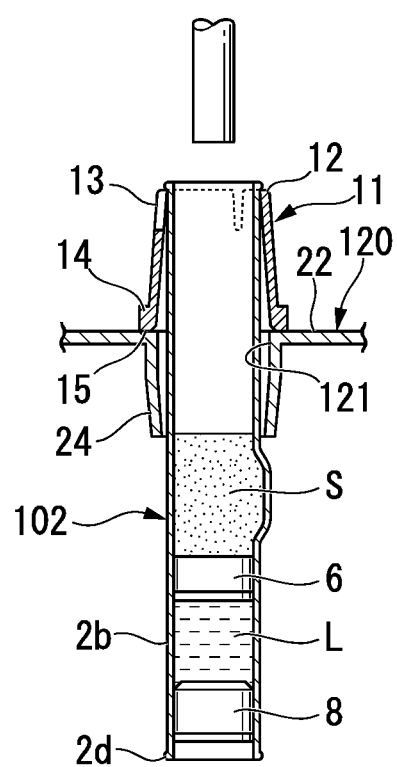
FIG. 27A is a view illustrating another example of powder filling related to the second embodiment.
Figure 27B:
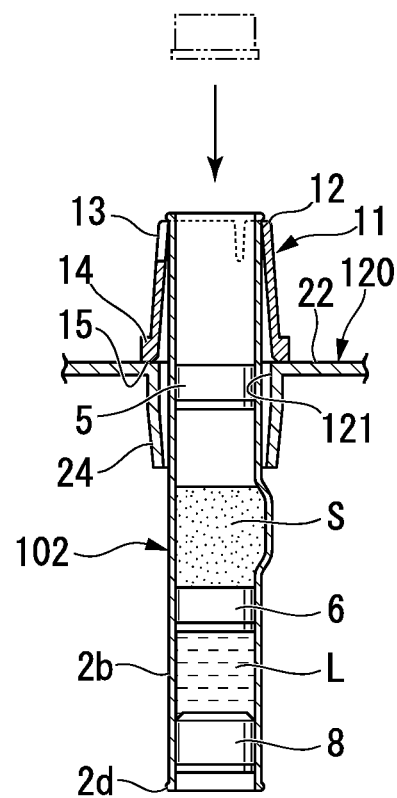
FIG. 27B is a view illustrating still another example of the powder filling related to the second embodiment.

Additionally, in the second embodiment, the example in which the injection drug solution sealed into the cartridge 2 in the injection drug sealing step S5 after the drug filling step S4 is made into a lyophilized preparation by the lyophilizing step S6 has been described. However, for example, a step of, as shown in FIG. 27A, filling the upper portion of the middle stopper 6 with a powdered drug from the upper end of the cartridge 102, and then, as shown in FIG. 27B, inserting the front stopper 5 into the cartridge 102 to seal the drug may be adopted.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A cartridge set for manufacturing a plurality of syringes each of which has a cartridge, a front assembly, a finger grip, a stopper, and a plunger rod, the cartridge set comprising:
the plurality of cartridges, each of the plurality of cartridges being part of a corresponding syringe, extending in an up-and-down direction, and forming a cylindrical shape having an outer peripheral surface, each opening end portion of the outer peripheral surface of each of the plurality of cartridges having an annular rib protruding radially outward;
a plurality of holders which are made of flexible material, each holder having an upper end disposed externally and removably around an abutting portion of the outer peripheral surface of a corresponding cartridge, said upper end defining an inner diameter of the holder that is equal to or smaller than the abutting portion of the outer peripheral surface of the corresponding cartridge to thereby exert a restoring force that retains the corresponding cartridge in the holder, each holder having a gradually increasing diameter in ad downward direction and having a lower end face whose outer diameter is greater than the outer diameter of the outer peripheral surface of the cartridge;
a supporting plate that forms a plate shape that extends in a horizontal direction, has a plurality of through-holes, each of which has an inner diameter greater than the outer diameter of the outer peripheral surface of the cartridge and has each of the plurality of cartridges inserted therethrough in the up-and-down direction, and has a top face on which the lower end faces of the plurality of holders are placed in a state where the plurality of cartridges are each inserted through the plurality of through-holes in the up-and-down direction, the supporting plate thereby supporting the plurality of holders and the corresponding cartridges around whose outer peripheral surfaces the upper ends of the holders are disposed;

a storage box that forms a box shape that opens upward, stores the supporting plate therein in a state where the supporting plate supports the plurality of cartridges via the plurality of holders, and has a supporting portion which supports an outer edge of the supporting plate; and a lid member that blocks an upper end opening of the storage box, wherein the annular rib protrudes radially outward from the outer diameter of the lower end face, wherein the plurality of holders, the supporting plate, the storage box, and the lid member are members separable from the plurality of syringe, and wherein the holder is removed from the outer peripheral surface of the cartridge after the front assembly is fitted to the cartridge.

2. The cartridge set according to claim 1,
wherein the holder has a slit that extends downward from the upper end of the holder.

3. A method for manufacturing a dual-chamber type combined container-syringe using the cartridge set having a plurality of cartridges, each of which extends in an up-and-down direction, forms a cylindrical shape having an outer peripheral surface, and has annular ribs protruding radially outward from opening end portions thereof that correspond to both ends of the outer peripheral surface; and a plurality of holders, each of which has flexibility, has an upper end externally fitted to the outer peripheral surface of each of the cartridges, is gradually increased in diameter as it goes downward, and has a lower end face whose outer diameter is greater than the outer diameter of the outer peripheral surface of the cartridge; and a supporting plate that forms a plate shape that extends in a horizontal direction, has a plurality of through-holes, each of which has an inner diameter greater than the outer diameter of the outer peripheral surface of the cartridge and has each of the plurality of cartridges inserted therethrough in the up-and-down direction, and has a top face on which the lower end faces of the plurality of holders are placed in a state where the plurality of cartridges are each inserted through the plurality of through-holes in the up-and-down direction; and a storage box that forms a box shape that opens upward, stores the supporting plate therein in a state where the supporting plate supports the plurality of cartridges via the plurality of holders, and has a supporting portion which supports an outer edge of the supporting plate; and a lid member that blocks an upper end opening of the storage box, the method comprising:

a first step of taking out the supporting plate along with the plurality of holders and the plurality of cartridges from the cartridge set;

a second step of, after the first step, sequentially filling and inserting an end stopper, a solvent, and a middle stopper into each of the plurality of cartridges from above in a state where the plurality of cartridges is supported by the supporting plate via the plurality of holders, and sealing the solvent within the cartridge;

a third step of, after the second step, inserting a drug and a front stopper into each of the plurality of cartridges from above, and sealing the drug within the cartridge; and a holder removing step of removing the plurality of holders from the outer peripheral surfaces of the plurality of cartridges.

4. The method for manufacturing a dual-chamber type combined container-syringe according to claim 3,
wherein the third step includes:
a filling step of filling an injection drug solution into each of the plurality of cartridges;
a sealing step of sealing the injection drug solution along with an internal gas within the cartridge by the middle stopper and the front stopper; and
a lyophilizing step of lyophilizing the injection drug solution to make the injection drug solution into a lyophilized preparation as the drug, and
wherein the lyophilizing step includes:
a freezing process of freezing the injection drug solution;
a pressure-reducing process of, after the freezing process, making the pressure of an external atmosphere lower than the pressure of the internal gas within the cartridge to bring the front stopper into a partially closed state with respect to the cartridge;
a drying process of changing the injection drug solution to the lyophilized preparation due to a sublimation action;
a replacement process of replacing the internal gas within the cartridge with pure nitrogen; and
a sealing process of pushing the front stopper in the partially closed state into the cartridge.

5. The method for manufacturing a dual-chamber type combined container-syringe according to claim 3, further comprising, between the second step and the third step, a autoclave sterilization step of exposing the plurality of cartridges to steam in a state where the plurality of cartridges is supported by the supporting plate via the plurality of holders.

6. The method for manufacturing a dual-chamber type combined container-syringe according to claim 3, further comprising, after the third step, a front assembly fitting step of removing the plurality of cartridges, to each of which a corresponding one of the plurality of holders is fitted, from the supporting plate, and externally fitting each of a plurality of front assemblies to a corresponding one of the plurality of cartridges while each of the plurality of holders is pressed downward by a corresponding one of the plurality of front assemblies.

7. The method for manufacturing a dual-chamber type combined container-syringe according to claim 6, wherein the holder removing step is performed after the front assembly fitting step, and includes moving the plurality of holders downward relative to the plurality of cartridges to remove each of the plurality of holders from lower sides of the plurality of cartridges.

* * * * *